US011746147B2

(12) United States Patent
Lu et al.

(10) Patent No.: US 11,746,147 B2
(45) Date of Patent: Sep. 5, 2023

(54) ANGIOPOIETIN 2, VEGF DUAL ANTAGONISTS

(71) Applicants: AskGene Pharma Inc., Camarillo, CA (US); Jiangsu Aosaikang Pharmaceutical Co., Ltd., Nanjing (CN)

(72) Inventors: Yuefeng Lu, Newbury Park, CA (US); Jian-Feng Lu, Oak Park, CA (US)

(73) Assignees: AskGene Pharma Inc., Camarillo, CA (US); Jiangsu Aosaikang Pharmaceutical Co., Ltd., Nanjing (CN)

( * ) Notice: Subject to any disclaimer, the term of this patent is extended or adjusted under 35 U.S.C. 154(b) by 489 days.

(21) Appl. No.: 16/741,686

(22) Filed: Jan. 13, 2020

(65) Prior Publication Data
US 2020/0131260 A1 Apr. 30, 2020

Related U.S. Application Data

(62) Division of application No. 15/593,280, filed on May 11, 2017, now Pat. No. 10,654,922.

(51) Int. Cl.
*C07K 16/22* (2006.01)
*C07K 14/515* (2006.01)
*C07K 14/71* (2006.01)
*A61K 39/00* (2006.01)

(52) U.S. Cl.
CPC ............ *C07K 16/22* (2013.01); *C07K 14/515* (2013.01); *C07K 14/71* (2013.01); *A61K 2039/505* (2013.01); *C07K 2317/14* (2013.01); *C07K 2317/51* (2013.01); *C07K 2317/515* (2013.01); *C07K 2317/76* (2013.01); *C07K 2317/92* (2013.01); *C07K 2319/30* (2013.01); *C07K 2319/32* (2013.01); *C07K 2319/70* (2013.01)

(58) Field of Classification Search
None
See application file for complete search history.

(56) References Cited

U.S. PATENT DOCUMENTS

| | | | | |
|---|---|---|---|---|
| 7,138,370 B2 * | 11/2006 | Oliner | ...................... | C07K 7/06 |
| | | | | 514/21.4 |
| 9,045,545 B1 * | 6/2015 | Clube | .................. | C12Q 1/6883 |
| 10,654,922 B2 * | 5/2020 | Lu | ......................... | C07K 14/515 |
| 11,059,885 B2 * | 7/2021 | Lu | ............................ | A61K 9/08 |
| 2016/0143852 A1 * | 5/2016 | Callahan | ................ | A61K 38/10 |
| | | | | 424/134.1 |

OTHER PUBLICATIONS

Burgess et al., Journal of Cell Biology, vol. 111, pp. 2129-2138 (Year: 1990).*
Lazar et al., Molecular and Cellular Biology, vol. 8, pp. 1247-1252 (Year: 1988).*
Rudikoff et al., Proc Natl Acad Sci USA 1982 vol. 79 p. 1979-1983 (Year: 1982).*
Piche-Nicholas et al., MABS 10(1): 81-94 (Year: 2018).*

* cited by examiner

*Primary Examiner* — Phuong Huynh
(74) *Attorney, Agent, or Firm* — ENTRALTA P.C.; James F. Fleming; Peter D. Weinstein

(57) ABSTRACT

The present disclosure relates to chimeric molecules which are fusion proteins comprising two components: an Ang-2 binding peptide linked to either a VEGF antibody or a VEGF receptor-Fc fusion protein. The Ang2 peptide, VEGF antibody, and VEGF receptor-Fc fusion proteins are each defined below with reference to percent identity to a reference sequence. The chimeric molecule is a fusion protein, dual antagonist of Ang2 and VEGF for treatment of cancers, proliferative retinopathies, neovascular glaucoma, macular edema, AMD, and rheumatoid arthritis.

5 Claims, 5 Drawing Sheets

Specification includes a Sequence Listing.

ANGIOPOIETIN 2, VEGF DUAL ANTAGONISTS

CROSS-REFERENCE TO RELATED APPLICATIONS

The present application is a divisional application of U.S. application Ser. No. 15/593,280 filed May 11, 2017 (now U.S. Pat. No. 10,654,922) and claims priority to U.S. Provisional Patent Application 62/336,522, filed May 13, 2016, Provisional Patent Application 62/448,998, filed Jan. 21, 2017, and Provisional Patent Application 62/459,046, filed Feb. 14, 2017, herein each incorporated by reference in their entirety.

REFERENCE TO SEQUENCE LISTING

The entire content of the following electronic submission of the sequence listing via the USPTO EFS-WEB server, as authorized and set forth in MPEP § 1730 II.B.2(a)(C), is hereby expressly incorporated by reference in its entirety for all purposes. The sequence listing is identified on the electronically filed text file as follows: File Name: 3IPAG3-0006USD1-Sequense-ListingST25; Date of Creation: May 10, 2017; Size (bytes): 52 KB.

INTRODUCTION

Angiogenesis is implicated in the pathogenesis of a variety of disorders including solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al, Annu. Rev. Physiol. 53 (1991) 217-239; and Garner, A., Vascular Diseases, in: Pathobiology of Ocular Disease, A Dynamic Approach, Garner, A., and Klintworth, G. K. (eds.), 2nd edition, Marcel Dekker, New York (1994), pp. 1625-1710). In the case of solid tumors, the neovascularization allows the tumor cells to acquire a growth advantage and proliferative autonomy compared to the normal cells. Accordingly, a correlation has been observed between density of microvessels in tumor sections and patient survival in a number of cancers (see, e.g., Weidner, N., et al, N Engl J Med. 324 (1991) 1-8; Horak, E. R., et al, Lancet 340 (1992) 1120-1124; and Macchiarini, P., et al, Lancet 340 (1992) 145-146).

Human vascular endothelial growth factor (VEGF/VEGF-A) is described in, e.g., Leung, D. W., et al, Science 246 (1989) 1306-9; Keck, P. J., et al, Science 246 (1989) 1309-12 and Connolly, D. T., et al, J. Biol. Chem. 264 (1989) 20017-24. The expression of VEGF is potentiated in response to hypoxia, by activated oncogenes, and by a variety of cytokines. VEGF is involved in the regulation of normal and abnormal angiogenesis and neovascularization associated with tumors and intraocular disorders (Ferrara, N., et al, Endocr. Rev. 18 (1997) 4-25; Berkman, R. A., et al, J. Clin. Invest. 91 (1993) 153-159; Brown, L. F., et al, Human Pathol. 26 (1995) 86-91; Brown, L. F., et al, Cancer Res. 53 (1993) 4727-4735; Mattern, J., et al, Brit. J. Cancer. 73 (1996) 931-934; and Dvorak, H. F., et al, Am. J. Pathol. 146 (1995) 1029-1039).

Deregulated VEGF expression contributes to the development of solid tumors by promoting tumor angiogenesis and to the etiology of several additional diseases that are characterized by abnormal angiogenesis (Kim, K. J., et al., 1993. Nature (London) 362, 841-844; Millauer, B., et al., 1994. Nature (London) 367, 576-579). Consequently, inhibition of VEGF signaling abrogates the development of a wide variety of tumors.

In retinopathies, in which partial or general ischemia of the retina is accompanied by overexpression of VEGF and hyperproliferation of blood vessels, blindness can result (Aiello, L. P et al., 1994. N. Engl. J. Med. 331, 1480-1487; Adamis, A. P., et al., Am. J. Ophthalmol. 118, 445-450). Inhibition of VEGF expression in such disease states can treat or prevent resulting blindness.

Two VEGF receptors belonging to the tyrosine-kinase receptor family have been identified and cloned: the VEGFR-1 and the VEGFR-2 receptors (Devries, C. et al., 1992. Science 255, 989-991; Terman, B. I., et al., Biochem. Biophys. Res. Commun. 187, 1579-1586; Matthews, W., et al., 1991. Cell 65, 1143-1152; Shibuya, M., et al. 1990. Oncogene 5, 519-524). These receptors form a subfamily distinguished by the presence of seven immunoglobulin-like loops in their extracellular part and a split tyrosine-kinase domain in their intracellular part. The VEGFR-2 and VEGFR-1 receptors are expressed predominantly in endothelial cells, but a few additional types of cells express one or both of these receptors.

Efforts to inhibit VEGF-induced tumor angiogenesis include the development of humanized neutralizing anti-VEGF monoclonal antibodies (see, e.g., Presta, L. G. et al., Cancer Res. 57, 4593-4599 (1997); U.S. Pat. No. 6,884,879, WO 94/10202, WO 98/45332, WO 2005/00900 and WO 00/35956), and inhibitory soluble VEGF receptors (Kendall, R. L., and Thomas, K. A. Proc. Natl. Acad. Sci. USA 90, 10705-10709; Lin, P. N., et al., 1998. Cell Growth Differ. 9, 49-58). For example, the humanized monoclonal antibody bevacizumab (sold under the trade name Avastin®) is an anti-VEGF antibody used in tumor therapy (see, e.g., WO 98/45331). Ranibizumab (trade name Lucentis®) is a monoclonal antibody fragment derived from the same parent murine antibody as bevacizumab. It is much smaller than the parent molecule and has been affinity matured to provide stronger binding to VEGF-A (WO 98/45331). It is an anti-angiogenic that has been approved to treat the "wet" type of age-related macular degeneration (ARMD), a common form of age-related vision loss. Aflibercept is a recombinant fusion protein consisting of VEGF-binding portions from the extracellular domains of human VEGF receptors 1 and 2, that are fused to the Fc portion of the human IgG1 immunoglobulin.

Human angiopoietin-2 (ANG-2) (alternatively abbreviated with ANGPT2 or ANG2) is described in Maisonpierre, P. C., et al, Science 277 (1997) 55-60 and Cheung, A. H., et al, Genomics 48 (1998) 389-91. The angiopoietins-1 and -2 and were discovered as ligands for the Ties, a family of tyrosine kinases that is selectively expressed within the vascular endothelium. Yancopoulos, G. D., et al, Nature 407 (2000) 242-48. Ang-1 was shown to support EC survival and to promote endothelium integrity, Davis, S., et al, Cell 87 (1996) 1161-69; Kwak, H. J., et al, FEBS Lett 448 (1999) 249-53; Suri, C, et al, Science 282 (1998) 468-71; Thurston, G., et al, Science 286 (1999) 2511-2514; Thurston, G., et al, Nat. Med. 6 (2000) 460-63, whereas ANG-2 had the opposite effect and promoted blood vessel destabilization and regression in the absence of the survival factors VEGF or basic fibroblast growth factor. Maisonpierre, P. C., et al, Science 277 (1997) 55-60. However, many studies of ANG-2 function have suggested a more complex situation. ANG-2 might be a complex regulator of vascular remodeling that plays a role in both vessel sprouting and vessel regression.

In adult individuals, ANG-2 expression is restricted to sites of vascular remodeling as well as in highly vascularized tumors, including glioma, Osada, H., et al, Int. J. Oncol. 18 (2001) 305-09); Koga, K., et al, Cancer Res. 61 (2001) 6248-54, hepatocellular carcinoma, Tanaka, S., et al., J. Clin. Invest. 103 (1999) 341-45, gastric carcinoma, Etoh, T., et al, Cancer Res. 61 (2001) 2145-53; Lee, J. H., et al, Int. J. Oncol. 18 (2001) 355-61, thyroid tumor, Bunone, G., et al, Am J Pathol 155 (1999) 1967-76 non-small cell lung cancer, Wong, M. P., et al, Lung Cancer 29 (2000) 11-22, cancer of colon, Ahmad, S. A., et al, Cancer 92 (2001) 1138-43, and prostate cancer Wurmbach, J. H., et al., Anticancer Res. 20 (2000) 5217-20. By detecting ANG-2 niRNA levels in archived human breast cancer specimens, Sfiligoi, C, et al, Int. J. Cancer 103 (2003) 466-74 reported that ANG-2 mRNA is significantly associated with auxiliary lymph node invasion, short disease-free time and poor overall survival. Tanaka, F., et al., Cancer Res. 62 (2002) 7124-29 reviewed a total of 236 patients of non-small cell lung cancer (NSCLC) with pathological stage-I to -IIIA, respectively. Using immunohistochemistry, they found that 16.9% of the NSCLC patients were ANG-2 positive. The microvessel density for ANG-2 positive tumor is significantly higher than that of ANG-2 negative. Such an angiogenic effect of ANG-2 was seen only when VEGF expression was high. Moreover, positive expression of ANG-2 was a significant factor to predict a poor postoperative survival. Tanaka, F., et al, Cancer Res. 62 (2002) 7124-7129. These results suggest that ANG-2 is an indicator of poor prognosis patients with several types of cancer.

In recent years Angiopoietin-1, Angiopoietin-2 and/or Tie-2 have been proposed as possible anti-cancer therapeutic targets. For example, U.S. Pat. Nos. 6,166,185, 5,650,490 and 5,814,464 each disclose anti-Tie-2 ligand and receptor antibodies. Effective anti-Angiopoietin-2 therapy is thought to be of benefit in treating diseases such as cancer, in which progression is dependent on aberrant angiogenesis where blocking the process can lead to prevention of disease advancement (Folkman, J., Nature Medicine. 1 (1995) 27-31). In addition, some groups have reported the use of antibodies and peptides that bind to Angiopoietin-2, such as the peptides 2×Con4(C), L1-7, L1-10, and L1-15, as described in WO2004/092215 and WO2003/05134, and block the interaction between Angiopoietin-2 and Tie-2. According to WO2003/05134, 2×Con4(C) also bound to Angiopoietin-1 and inhibited its interaction with Tie-2, while peptides L1-7, L-10 and L1-15 had little affinity for Angiopoietin-1. For additional Ang2 binding peptides, see, for example, U.S. Pat. Nos. 6,166,185, 7,666,832, US 2003/10124129. WO 03/030833, WO 2006/068953, WO 03/057134 or US 2006/0122370.

A wide variety of recombinant antibody formats have been developed in the recent past, e.g., tetravalent bispecific antibodies by fusion of, e.g., an IgG antibody format and single chain domains (see e.g., Coloma, M. J., et al, Nature Biotech 15 (1997) 159-163; WO 2001/077342; and Morrison, S. L., Nature Biotech 25 (2007) 1233-1234).

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al, Nature Biotech 23 (2005) 1126-1136; Fischer, N., Leger, O., Pathobiology 74 (2007) 3-14; Shen, J., et al, Journal of Immunological Methods 318 (2007) 65-74; Wu, C, et al, Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N., Leger, O., Pathobiology 74 (2007) 3-14). It has to be kept in mind that one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

In WO 2007/024715 are reported dual variable domain immunoglobulins as engineered multivalent and multispecific binding proteins. A process for the preparation of biologically active antibody dimers is reported in U.S. Pat. No. 6,897,044. Multivalent $F_v$ antibody construct having at least four variable domains which are linked with each over via peptide linkers are reported in U.S. Pat. No. 7,129,330. Dimeric and multimeric antigen binding structures are reported in US 2005/0079170. Tri- or tetravalent monospecific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage from dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342.

Multispecific and multivalent antigen-binding polypeptides are reported in WO 1997/001580. WO 1992/004053 reports homoconjugates, typically prepared from monoclonal antibodies of the IgG class which bind to the same antigenic determinant are covalently linked by synthetic cross-linking. Oligomeric monoclonal antibodies with high avidity for antigen are reported in WO 1991/06305 whereby the oligomers, typically of the IgG class, are secreted having two or more immunoglobulin monomers associated together to form tetravalent or hexavalent IgG molecules. Sheep-derived antibodies and engineered antibody constructs are reported in U.S. Pat. No. 6,350,860, which can be used to treat diseases wherein interferon gamma activity is pathogenic. In US 2005/0100543 are reported targetable constructs that are multivalent carriers of bi-specific antibodies, i.e., each molecule of a targetable construct can serve as a carrier of two or more bi-specific antibodies. Genetically engineered bispecific tetravalent antibodies are reported in WO 1995/009917. In WO 2007/109254 stabilized binding molecules that consist of or comprise a stabilized scFv are reported.

Combination of VEGF and ANG-2 inhibitors in WO 2007/068895 refers to a combination of an ANG-2 antagonist and a VEGF, KDR and/or FLTL antagonist. WO 2007/089445 refers to ANG-2 and VEGF inhibitor combinations. WO 2003/106501 refers to fusion proteins binding to Angiopoietin and containing a multimerization domain. WO 2008/132568 relates to fusion proteins binding to Angiopoietin and VEGF. WO 2003/020906 relates to multivalent protein conjugates with multiple ligand-binding domains of receptors.

As opposed to the compositions described above, the present specification contemplates the use of a dual antagonist. The chimeric protein of the invention comprises an Ang2 binding peptide fused to either a VEGF antibody or a VEGF receptor-Fc fusion protein. The efficacy obtained with a dual antagonist of the present disclosure is synergistically improved in comparison to either the native protein antagonist/inhibitor or a construct directed to a single antagonist.

SUMMARY

In one aspect, the present invention provides a chimeric molecule comprising:
a. an anti-VEGF antibody or a VEGF receptor-Fc-fusion; and
b. a peptide that binds to angiopoietin 2 (Ang2);
c. wherein the peptide that binds to Ang2 comprises a sequence having at least 70%, at least 75%, at least 80%, at least 85%, at least 90%, at least 95%, at least 96%, at least 97%, at least 98%, at least 99% or 100% sequence identity to SEQ ID NO:1; and
d. wherein the chimeric molecule inhibits the binding of VEGF to a VEGF receptor and inhibits binding of Ang2 to an Ang2 receptor.

In one embodiment, the Ang2 binding peptide is fused to the C-terminus of the heavy chain of the anti-VEGF antibody, wherein the chimeric molecule also comprises a light chain.

In one embodiment, the anti-VEGF antibody comprises a heavy chain and a light chain, wherein the heavy chain comprising a sequence having at least 70%, at least 75%, at least 80%, at least 85%, at least 90%, at least 95%, at least 96%, at least 97%, at least 98%, at least 99% or 100% sequence identity to SEQ ID NO:2; and wherein the light chain comprises a sequence having at least 70%, at least 75%, at least 80%, at least 85%, at least 90%, at least 95%, at least 96%, at least 97%, at least 98%, at least 99% or 100% sequence identity to SEQ ID NO:3.

In one embodiment, the Ang2 binding peptide fused to the C-terminus of the heavy chain of the anti-VEGF antibody, wherein the chimeric molecule comprises a sequence having at least 70%, at least 75%, at least 80%, at least 85%, at least 90%, at least 95%, at least 96%, at least 97%, at least 98%, at least 99% or 100% sequence identity to SEQ ID NO:4 or SEQ ID NO:17; wherein the chimeric molecule also comprises a light chain comprises a sequence having at least 70%, at least 75%, at least 80%, at least 85%, at least 90%, at least 95%, at least 96%, at least 97%, at least 98%, at least 99% or 100% sequence identity to SEQ ID NO:3.

In one embodiment, the VEGF receptor-Fc fusion comprises a sequence having at least 70%, at least 75%, at least 80%, at least 85%, at least 90%, at least 95%, at least 96%, at least 97%, at least 98%, at least 99% or 100% sequence identity to SEQ ID NO:5.

In one embodiment, the polypeptide comprising the Ang2 binding peptide fused to the C-terminus of the VEGF-Fc fusion protein, wherein the chimeric molecule comprises a sequence having at least 70%, at least 75%, at least 80%, at least 85%, at least 90%, at least 95%, at least 96%, at least 97%, at least 98%, at least 99% or 100% sequence identity to SEQ ID NO:6.

In one embodiment, the Ang2 binding protein is fused to the C-terminus of the VEGF receptor-Fc fusion.

In one embodiment, the VEGF antibody is selected from a single-chain Fv antibody (scFv), a Fab antibody, a Fab' antibody, a (Fab')2 antibody, a domain antibody, a nanobody, a minibody, a maxibody, and a diabody.

In one aspect, the invention provides a chimeric molecule, which comprises an antibody and an Ang2 binding peptide, wherein said peptide is fused to the N-terminus or C-terminus of the light chains and/or heavy chains of said antibody, optionally with a peptide linker, wherein the peptide has an amino acid sequence with at least 80%, at least 85%, at least 90%, at least 95%, or 100% identity to a peptide selected from the group consisting of SEQ ID NOS:7-12, and wherein said antibody binds to VEGF.

In one embodiment, said antibody has a heavy chain with amino acid sequence at least 95% identity to that of SEQ ID NO:2, and light chain with amino acid sequence at least 95% identity to SEQ ID NO:3.

In one embodiment, the chimeric molecule comprises a peptide-light chain fusion with an amino acid sequence at least 98%, at least 99%, or 100% identical to SEQ ID NO 14, wherein said chimeric molecule further comprises a heavy chain with amino acid sequence at least 99% identical to that of SEQ ID NO:2.

In one embodiment, the chimeric molecule comprises a peptide-heavy chain fusion molecule with an amino acid sequence at least 98%, at least 99%, or 100% identical to SEQ ID NO 15 or SEQ ID NO 16, wherein said chimeric molecule further comprises a light chain with amino acid sequence at least 99% identical to that of SEQ ID NO:3.

In one embodiment, the chimeric molecule comprises a peptide-light chain fusion with an amino acid sequence at least 98%, at least 99%, or 100% identical to SEQ ID NO:14, wherein it further comprises a peptide-heavy chain fusion molecule with an amino acid sequence at least 98%, at least 99%, or 100% identical to SEQ ID NO:15 or SEQ ID NO:16.

In one embodiment, said peptide is fused to the N-terminal or C-terminal of said protein, optionally with a peptide linker, wherein the peptide has an amino acid sequence with at 80%, at least 85%, at least 90%, at least 95%, or 100% identity to a peptide selected from the group consisting of SEQ ID NOS:7-12, and wherein said protein has an amino acid sequence of at least 95% identity to that of SEQ ID NO:5.

In one embodiment, the fusion molecule forms a homologous dimer, and wherein the dimer binds to both VEGF and Ang 2.

In one aspect, the invention provides polynucleotides encoding the chimeric molecules described above, an expression vector comprising the polynucleotide, a host cell transfected with the vector, and a method of producing a chimeric molecule comprising culturing the host cell.

In one aspect the invention provides a pharmaceutical composition comprising a chimeric molecules and a pharmaceutically acceptable carrier.

In one aspect, the invention provides a method of treating cancer, proliferative retinopathy, age-related macular degeneration or rheumatoid arthritis comprising administering to a subject a pharmaceutical composition as described above.

In one embodiment, the cancer is selected from the group consisting of colon, lung, breast, renal and brain cancer.

DETAILED DESCRIPTION OF THE INVENTION

Figure 1:
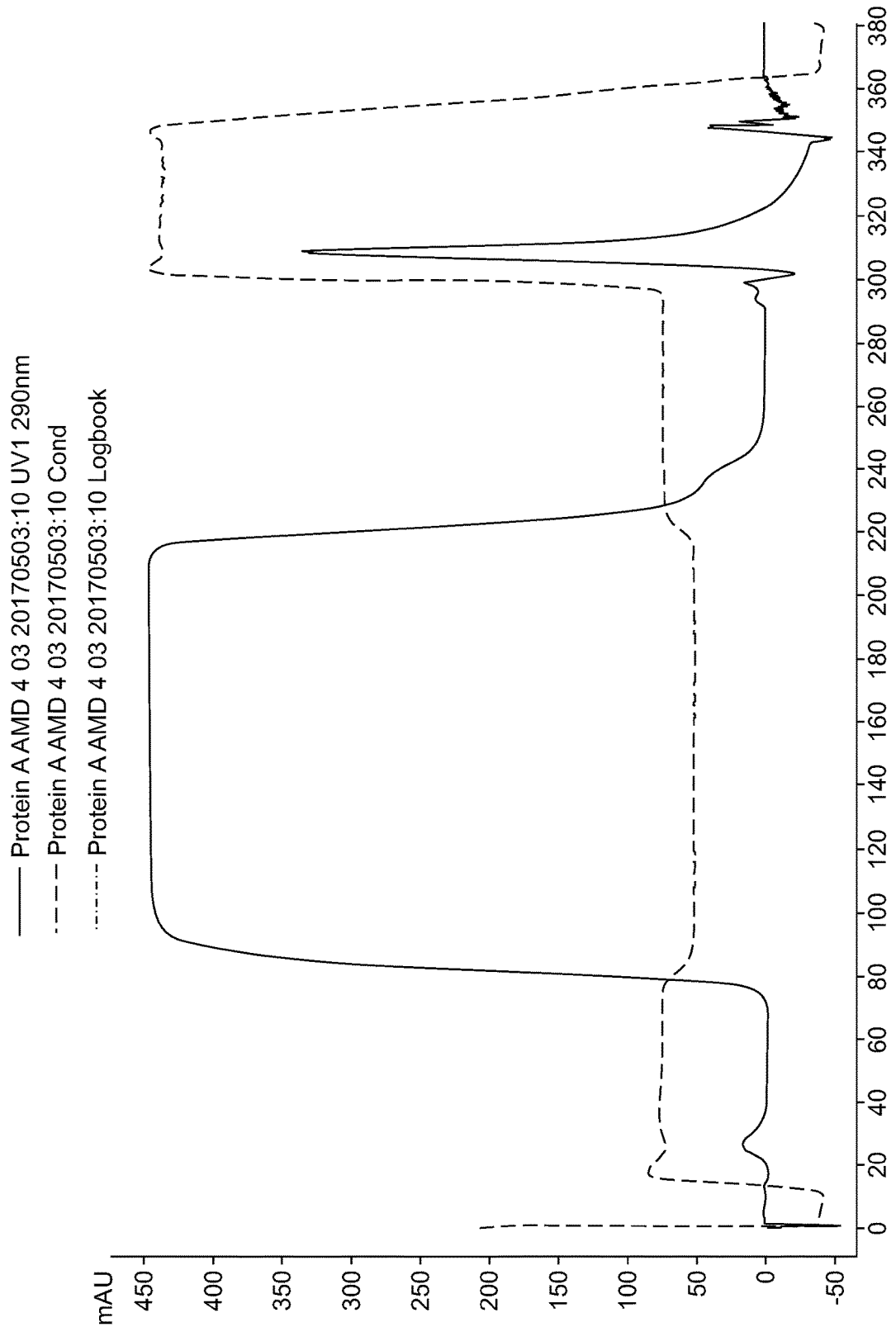
FIG. 1. Protein A Affinity Chromatography. Approximately 150 ml of the clarified HEK 293 cell culture medium of the transient expression of AMD-B was loaded to a Protein A column (1×17 cm (Diameter×Height) of Captiv A Protein A resin) at 3 ml/min. The protein A column was equilibrated with an equilibration buffer (25 mM Tris Buffer, 100 mM NaCl, PH approximately 7.2). The column was washed with the Equilibration buffer and eluted with 2 M ariginine solution, PH 4.

Disclosed herein are chimeric proteins which are fusion proteins comprising two components: an Ang-2 binding peptide linked to either a VEGF antibody or a VEGF receptor-Fc fusion protein. The Ang2 peptide, VEGF antibody, and VEGF receptor-Fc fusion proteins are each defined below with reference to percent identity to a reference sequence. The chimeric protein is a fusion protein, dual antagonist of Ang2 and VEGF for treatment of cancers, proliferative retinopathies, neovascular glaucoma, macular edema, AMD, and rheumatoid arthritis.

The chimeric protein comprises a Ang2 peptide component, which binds to Angiopoietin 2 (Ang2) and inhibits the binding of Ang2 to its receptor. One example of the peptide is called 2×Con4(C), as described in WO2004/092215A2 or WO03/05134A2. 2×Con4(C) has an amino acid sequence as shown in SEQ ID NO:1. Additional examples of Ang2 binding peptides include but are not limited to: L1-7, L1-10, and L1-15, as described in WO2004/092215A2. Those peptides have amino acid sequences as shown in SEQ ID NO: 7-9.

The chimeric protein comprises one of two additional components. The first of the additional components is a VEGF antibody that inhibits the binding of VEGF to its receptors. One example of the VEGF antibody is bevacizumab, which has two heavy chains with amino acid sequence as shown as SEQ ID NO:2, and two light chains with amino acid sequence as shown as SEQ ID NO:3.

The second of the additional components is a VEGF receptor-Fc fusion protein which "traps" VEGF and competes with the naturally occurring VEGF cellular receptor to inhibit VEGF. One example of the VEGF-receptor Fc fusion protein is afilbercept, which has an amino acid sequence as shown in SEQ ID NO:5.

The fusion proteins can be made entirely through recombinant expression with or without amino acid linkers between the components of the chimeric protein; alternatively, they can be made with or without linkers through protein native chemical ligation (NCL) or site specific conjugation, wherein the peptide is chemically synthesized and the VEGF antibody or the VEGF receptor-Fc fusion protein molecules are recombinant expressed.

The Ang2 peptide can be linked or fused to either the C- or N-terminus of the VEGF antibody (e.g., either the heavy or the light chains) or the VEGF receptor-Fc fusion protein. The Fc portion of the VEGF receptor-Fc fusion protein may be located at either the C- or N-terminus of the VEGF receptor protein. The Fc portion is further defined herein.

The resulting molecules possess dual-antagonist activities and have therapeutic effects for cancers, proliferative retinopathies, diabetic retinopathies, age-related macular degeneration and rheumatoid arthritis.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing, isolating, purifying, synthesizing, and recombinantly manufacturing) polypeptides are well known to one of ordinary skill in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The present composition encompasses amino acid substitutions in proteins and peptides, which do not generally alter the activity of the proteins or peptides (H. Neurath, R. L. Hill, The Proteins, Academic Press, New York, 1979). In one embodiment, these substitutions are "conservative" amino acid substitutions. The most commonly occurring substitutions are Ala/Ser, Val/Ile, Asp/Glu, Thr/Ser, Ala/Gly, Ala/Thr, Ser/Asn, Ala/Val, Ser/Gly, Ala/Pro, Lys/Arg, Asp/Asn, Leu/Ile, Leu/Val, Ala/Glu and Asp/Gly, in both directions As to "conservatively modified variants" of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Analogue as used herein denotes a peptide, polypeptide, or protein sequence which differs from a reference peptide, polypeptide, or protein sequence. Such differences may be the addition, deletion, or substitution of amino acids, phosphorylation, sulfation, acrylation, glycosylation, methylation, farnesylation, acetylation, amidation, and the like, the use of non-natural amino acid structures, or other such modifications as known in the art.

The term "unnatural amino acids" as used herein refers to amino acids other than the 20 typical amino acids found in the proteins in our human body. Unnatural amino acids are non-proteinogenic amino acids that either occur naturally or are chemically synthesized. They may include but are not limited to aminoisobutyric acid (Aib), β-amino acids ($β^3$ and $β^2$), homo-amino acids, Proline and Pyruvic acid derivatives, 3-substituted Alanine derivatives. Glycine derivatives, Ring-substituted Phenylalanine and Tyrosine derivatives, Linear core amino acids, diamino acids, D-amino acids and N-methyl amino acids.

Further an N-terminal amino acid may be modified by coupling an imidazolic group to the N-terminal amino acid of a polypeptide. Such imidzolic groups can be 4-imidazopropionyl (des-amino-histidyl), 4-amidzoacetyl, 5-imidazo-α, α dimethyl-acetyl. Coupling the imidazolic group to the present fusion peptide or portions thereof may be accomplished by synthetic chemical means. Because many of the various organic groups contemplated herein contain a carboxylic acid, the imidazolic group can be added by solid phase protein synthesis analogous to adding an amino acid to the N-terminus of a polypeptide. Alternatively, an activated ester of the imidazolic group can be added by standard chemical reaction methods. Notation for these imidazolic groups may be denoted by "CA-" appearing prior to the N-terminal of a peptide or protein. In one embodiment, the imidazolic group is a 4-imidzoacetyl group.

An Ang2 peptide of the invention is a peptide that binds to Ang2 protein and comprises a sequence having at least 70%, at least 75%, at least 80%, at least 85%, at least 90%, at least 95%, at least 96%, at least 97%, at least 98%, at least 99% or 100% sequence identity to SEQ ID NO:1.

The anti-VEGF antibody of the invention may comprise a heavy chain and a light chain, wherein the heavy chain comprising a sequence having at least 70%, at least 75%, at least 80%, at least 85%, at least 90%, at least 95%, at least 96%, at least 97%, at least 98%, at least 99% or 100% sequence identity to SEQ ID NO:2; and wherein the light chain comprises a sequence having at least 70%, at least 75%, at least 80%, at least 85%, at least 90%, at least 95%, at least 96%, at least 97%, at least 98%, at least 99% or 100% sequence identity to SEQ ID NO:3.

A VEGF receptor-Fc fusion protein of the invention is a sequence having at least 70%, at least 75%, at least 80%, at least 85%, at least 90%, at least 95%, at least 96%, at least 97%, at least 98%, at least 99% or 100% sequence identity to SEQ ID NO:5.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H 1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

Accordingly, in either aspect of the invention, the term antibody also embraces minibodies, diabodies, triabodies and the like. Diabodies are small bivalent biospecific antibody fragments with high avidity and specificity. Their high signal to noise ratio is typically better due to a better specificity and fast blood clearance increasing their potential for diagnostic and therapeutic targeting of specific antigen (Sundaresan et al., J Nucl Med 44:1962-9 (2003). In addition, these antibodies are advantageous because they can be engineered if necessary as different types of antibody fragments ranging from a small single chain Fv to an intact IgG with varying isoforms (Wu & Senter, Nat. Biotechnol. 23:1137-1146 (2005)). In some embodiments, the antibody fragment is part of a diabody. In some embodiments, in either aspect, the invention provides high avidity antibodies for use according to the invention.

In some embodiments, the present invention provides anti-VEGF sequences comprising CDR regions of SEQ ID NOS: 2 and 3 or a sequence having at least 70%, at least 75%, at least 80%, at least 85%, at least 90%, at least 95%, at least 96%, at least 97%, at least 98%, at least 99% or 100% sequence identity to SEQ ID NO:2 or 3. The CDR regions provided by the invention may be used to construct an anti-VEGF binding protein, including without limitation, an antibody, a scFv, a triabody, a diabody, a minibody, and the like. In a certain embodiment, an anti-VEGF binding protein of the invention will comprise at least one CDR region from SEQ ID NOS: 2 or 3 or a sequence having at least 70%, at least 75%, at least 80%, at least 85%, at least 90%, at least 95%, at least 96%, at least 97%, at least 98%, at least 99% or 100% sequence identity to SEQ ID NOS: 2 or 3. Anti-VEGF binding proteins may comprise, for example, a CDR-H1, a CDR-H2, a CDR-H3, a CDR-L1, a CDR-L2, a CDR-L3, or combinations thereof, from an antibody provided herein. In particular embodiments of the invention, an anti-VEGF binding protein may comprise all three CDR-H sequences of an antibody provided herein, all three CDR-L sequences of an antibody provided herein, or both. Anti-VEGF CDR sequences may be used on an antibody backbone, or fragment thereof, and likewise may include humanized antibodies, or antibodies containing humanized sequences. In some embodiments, the CDR regions may be defined using the Kabat definition, the Chothia definition, the AbM definition, the contact definition, or any other suitable CDR numbering system.

In some embodiments, the invention provides antibodies (e.g., diabodies, minibodies, triabodies) or fragments thereof having the CDRs of SEQ ID NOS: 2 or 3 or a sequence having at least 70%, at least 75%, at least 80%, at least 85%, at least 90%, at least 95%, at least 96%, at least 97%, at least 98%, at least 99% or 100% sequence identity to SEQ ID NOS: 2 or 3. In other embodiments, the diabodies possess the light and heavy chain of SEQ ID NOS: 2 and 3 or a sequence having at least 70%, at least 75%, at least 80%, at least 85%, at least 90%, at least 95%, at least 96%, at least 97%, at least 98%, at least 99% or 100% sequence identity to SEQ ID NOS: 2 or 3.

Diabodies, first described by Hollinger et al., PNAS (USA) 90(14): 6444-6448 (1993), may be constructed using heavy and light chains disclosed herein, as well as by using individual CDR regions disclosed herein. Typically, diabody fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VH and VL domains of another fragment, thereby forming two antigen-binding sites. Triabodies can be similarly constructed with three antigen-binding sites. An Fv fragment contains a complete antigen-binding site which includes a VL domain and a VH domain held together by non-covalent interactions. Fv fragments embraced by the present invention also include constructs in which the VH and VL domains are crosslinked through glutaraldehyde, intermolecular disulfides, or other linkers. The variable domains of the heavy and light chains can be fused together to form a single chain variable fragment (scFv), which retains the original specificity of the parent immunoglobulin. Single chain Fv (scFv) dimers, first described by Gruber et al., J. Immunol. 152(12):5368-74 (1994), may be constructed using heavy and light chains disclosed herein, as well as by using individual CDR regions disclosed herein. Many techniques known in the art can be used to prepare the specific binding constructs of the present invention (see, U.S. Patent Application Publication No. 20070196274 and U.S. Patent Application Publication No. 20050163782, which are each herein incorporated by reference in their entireties for all purposes, particularly with respect to minibody and diabody design).

Bispecific antibodies can be generated by chemical cross-linking or by the hybrid hybridoma technology. Alternatively, bispecific antibody molecules can be produced by recombinant techniques. Dimerization can be promoted by reducing the length of the linker joining the VH and the VL domain from about 15 amino acids, routinely used to produce scFv fragments, to about 5 amino acids. These linkers favor intrachain assembly of the VH and VL domains. Any suitable short linker can be used. Thus, two fragments assemble into a dimeric molecule. Further reduction of the linker length to 0-2 amino acids can generate trimeric (triabodies) or tetrameric (tetrabodies) molecules.

For preparation of antibodies, e.g., recombinant, monoclonal, or polyclonal antibodies, many techniques known in the art can be used (see, e.g., Kohler & Milstein, Nature 256:495-497 (1975); Kozbor et al., Immunology Today 4:72 (1983); Cole et al., in Monoclonal Antibodies and Cancer Therapy, Alan R. Liss, Inc., pp. 77-96 (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3.sup.rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., Nature 321:522-525 (1986); Riechmann et al., Nature 332: 323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

Construction of suitable vectors containing the desired sequences and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher et al., J. Biol. Chem. 273(52):35095-35101 (1998).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Cancer" refers to human cancers and carcinomas, sarcomas, adenocarcinomas, etc., including solid tumors, kidney, breast, lung, kidney, bladder, urinary tract, urethra, penis, vulva, vagina, cervical, colon, ovarian, prostate, pancreas, stomach, brain, head and neck, skin, uterine, testicular, esophagus, and liver cancer.

Proliferative retinopathy refers to diabetic proliferative retinopathy caused by type I or II diabetes.

AMD or age-related macular degeneration refers to both wet and dry forms of the disease.

In any of the embodiments above, one or more chemotherapeutic drug and/or cancer therapy, e.g., radiation therapy can be administered further with the chimeric protein of the invention. In one embodiment the chimeric protein of the invention is administered in the same course of therapy as 5FU, leucovorin, oxaliplatin and/or irinolecan or any subcombination thereof. In some embodiments, the patient also receives hormone antagonist therapy. The contacting of the patient with the antibody or antibody fragment, can be by administering the antibody to the patient intravenously, intraperitoneally, intramuscularly, intratumorally, or intradermally.

The present chimeric, fusion proteins may act as a dual receptor antagonist. The term "dual antagonist" or "dual co-antagonist" as used herein refers to a peptide or a fusion protein fusion protein which is capable of inhibiting Ang2 and VEGF.

The present compositions include "Fc fragments" or "Fc regions." The term "Fc fragment" or "immunoglobulin Fc region" as used herein, refers to a protein that contains at least the heavy-chain constant region 2 (CH2) and the heavy-chain constant region 3 (CH3) of an immunoglobulin. In one embodiment, the Fc region excludes the variable regions of the heavy and light chains, the heavy-chain constant region 1 (CH1) and the light-chain constant region 1 (CL1) of the immunoglobulin. The Fc region may further include a hinge region at the heavy-chain constant region. Also, the immunoglobulin Fc region disclosed herein may contain a part or all of the Fc region including the heavy-chain constant region 1 (CH1) and/or the light-chain constant region 1 (CL1), except for the variable regions of the heavy and light chains, as long as it has a physiological function substantially similar to or better than the native protein. Also, the immunoglobulin Fc region may be a fragment having a deletion in a relatively long portion of the amino acid sequence of CH2 and/or CH3. That is, the immunoglobulin Fc region disclosed herein may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

The immunoglobulin Fc region disclosed herein includes a native amino acid sequence, or a sequence analogue thereof. An amino acid sequence analogue is a sequence that is different from the native amino acid sequence due to a deletion, an insertion, a non-conservative or conservative substitution or combinations thereof of one or more amino acid residues.

Also, other various analogues are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site and an ADCC (antibody dependent cell mediated cytotoxicity) site. Techniques of preparing such sequence analogues of the immunoglobulin Fc region are disclosed in WO 1997/034631 and WO 1996/032478.

The aforementioned Fc analogues are analogues that have a biological activity identical to the Fc region disclosed herein or improved structural stability, for example, against heat, pH, or the like.

In addition, these Fc regions may be obtained from native forms isolated from humans and other animals including cows, goats, pigs, mice, rabbits, hamsters, rats and guinea pigs, or may be recombinants or analogues thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size exclusion chromatography to isolate Fc or pF'c. Preferably, a human-derived Fc region is a recombinant immunoglobulin Fc region that is obtained from a microorganism.

In one embodiment, the Fc region, if desired, may be modified by phosphorylation, sulfation, acrylation, glycosylation, methylation, farnesylation, acetylation, amidation, and the like. In one embodiment, the immunoglobulin Fc region disclosed herein may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the C1q part of the first complement component C1 and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable as a drug carrier.

As used herein, the term "deglycosylation" refers to enzymatically removing sugar moieties from an Fc region, and the term "aglycosylation" means that an Fc region is produced in an unglycosylated form by a prokaryote, preferably E. coli.

In one embodiment, the immunoglobulin Fc region may be an Fc region that is derived from IgG, IgA, IgD, IgE and IgM, or that is made by combinations thereof or hybrids thereof. Preferably, it is derived from IgG or IgM, which are among the most abundant proteins in human blood, and most preferably from IgG, which is known to enhance the half-lives of ligand-binding proteins.

The present chimeric fusion peptides may include a linker. In one embodiment, the linker is a peptide that ranges from about 6 to about 30 amino acids in length. In aspects of this embodiment, the peptide linker can be, e.g., at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or at least 30 amino acids in length. In other aspects of this embodiment, the peptide linker can be, e.g., at most 6, at most 7, at most 8, at most 9, at most 10, at most 11, at most 12, at most 13, at most 14, at most 15, at most 16, at most 17, at most 18, at most 19, at most 20, at most 21, at most 22, at most 23, at most 24, at most 25, at most 26, at most 27, at most 28, at most 29 or at most 30 amino acids in length. In other aspects of this embodiment, the peptide linker can be, e.g., about 6 to about 8, about 6 to about 10, about 6 to about 12, about 6 to about 14, about 6 to about 16, about 6 to about 18, about 6 to about 20, about 6 to about 22, about 6 to about 24, about 6 to about 26, about 6 to about 28, about 6 to about 30, about 8 to about 10, about 8 to about 12, about 8 to about 14, about 8 to about 16, about 8 to about 18, about 8 to about 20, about 8 to about 22, about 8 to about 24, about 8 to about 26, about 8 to about 28, about 8 to about 30, about 10 to about 12, about 10 to about 14, about 10 to about 16, about 10 to about 18, about 10 to about 20, about 10 to about 22, about 10 to about 24, about 10 to about 26, about 10 to about 28, about 10 to about 30, about 12 to about 14, about 12 to about 16, about 12 to about 18, about 12 to about 20, about 12 to about 22, about 12 to about 24, about 12 to about 26, about 12 to about 28, about 12 to about 30, about 14 to about 16, about 14 to about 18, about 14 to about 20, about 14 to about 22, about 14 to about 24, about 14 to about 26, about 14 to about 28, about 14 to about 30, about 16 to about 18, about 16 to about 20, about 16 to about 22, about 16 to about 24, about 16 to about 26, about 16 to about 28, about 16 to about 30, about 18 to about 20, about 18 to about 22, about 18 to about 24, about 18 to about 26, about 18 to about 28, about 18 to about 30, about 20 to about 22, about 20 to about 24, about 20 to about 26, about 20 to about 28, about 20 to about 30, about 22 to about 24, about 22 to about 26, about 22 to about 28, about 22 to about 30, about 24 to about 26, about 24 to about 28, about 24 to about 30, about 26 to about 28, about 26 to about 30 or about 26 to about 30 amino acids in length.

The term "native chemical ligation" (or NCL) as used herein refers to a concept for constructing a large polypeptide formed by the assembling of two or more unprotected peptides segments. Especially, NCL is the most powerful ligation method for synthesizing native backbone proteins or modified proteins.

The term "site specific conjugation" as used herein refers to a concept where a reaction group on a chemically synthesized peptide reacts specifically to a specific group of an Fc fragment produced through the recombinant technology. For example, a peptide contains an aldehyde group can react with the 1,2-aminothiol of cysteine of a recombinant Fc fragment through site-specific thiazolidine formation, as described by Zhang and Tam, "Thiazolidine formation as a general and site-specific conjugation method for synthetic peptides and proteins." Anal. Biochem. 1996 Jan. 1; 233(1): 87-93. Such chemically synthesized peptides may contain an aldehyde group. When the Fc region is chemically synthesized, the N-terminal amino acid of the Fc analogue may be modified to Cys, allowing site specific conjugation of the peptide to the Fc region.

The term "refolding" as used herein refers to the process by which a protein structure assumes its functional shape or conformation. It is the physical process by which a polypeptide folds into its characteristic and functional three-dimensional structure from random coil. It takes place at a basic pH (typically pH 8.0-10.0, pH 8.5-10, or pH 8.5-9.6), a low temperature (typically 0.0° C. to 10.0° C. or 2.0° C. to 8.0° C.), preferably with the presence of a redox pair at suitable concentrations, and/or at the presence of oxygen, and/or at the presence of catalyst(s) such as copper ions at suitable concentration.

The term "recombinant" as used herein refers to a polypeptide produced through a biological host, selected from a mammalian expression system, an insect cell expression system, a yeast expression system, and a bacterial expression system.

The term "formulation" as used herein refers to the fusion proteins disclosed herein and excipients combined together which can be administered and has the ability to bind to the corresponding receptors and initiate a signal transduction pathway resulting in the desired activity. The formulation can optionally comprise other agents so long as the fusion protein retains the ability to bind the corresponding receptors.

The present specification also provides a pharmaceutical composition for the administration to a subject. The pharmaceutical composition disclosed herein may further include a pharmaceutically acceptable carrier, excipient, or diluent. As used herein, the term "pharmaceutically acceptable" means that the composition is sufficient to achieve the therapeutic effects without deleterious side effects, and may be readily determined depending on the type of the diseases, the patient's age, body weight, health conditions, gender, and drug sensitivity, administration route, administration mode, administration frequency, duration of treatment, drugs used in combination or coincident with the composition disclosed herein, and other factors known in medicine.

The pharmaceutical composition including the fusion protein disclosed herein may further include a pharmaceutically acceptable carrier. For oral administration, the carrier may include, but is not limited to, a binder, a lubricant, a disintegrant, an excipient, a solubilizer, a dispersing agent, a stabilizer, a suspending agent, a colorant, and a flavorant. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The disclosed compositions may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

On the other hand, examples of the carrier, the excipient, and the diluent suitable for the pharmaceutical formulations include, without limitation, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

Further, the pharmaceutical composition disclosed herein may have any formulation selected from the group consisting of tablets, pills, powders, granules, capsules, suspensions, liquids for internal use, emulsions, syrups, sterile aqueous solutions, non-aqueous solvents, lyophilized formulations and suppositories.

Further, the composition may be formulated into a single dosage form suitable for the patient's body, and preferably is formulated into a preparation useful for peptide drugs according to the typical method in the pharmaceutical field so as to be administered by an oral or parenteral route such as through skin, intravenous, intramuscular, intra-arterial, intramedullary, intramedullary, intraventricular, pulmonary, transdermal, subcutaneous, intraperitoneal, intranasal, intracolonic, topical, sublingual, vaginal, or rectal administration, but is not limited thereto.

The composition may be used by blending with a variety of pharmaceutically acceptable carriers such as physiological saline or organic solvents. In order to increase the stability or absorptivity, carbohydrates such as glucose, sucrose or dextrans, antioxidants such as ascorbic acid or glutathione, chelating agents, low molecular weight proteins or other stabilizers may be used.

The administration dose and frequency of the pharmaceutical composition disclosed herein are determined by the type of active ingredient, together with various factors such as the disease to be treated, administration route, patient's age, gender, and body weight, and disease severity.

The total effective dose of the compositions disclosed herein may be administered to a patient in a single dose, or may be administered for a long period of time in multiple doses according to a fractionated treatment protocol. In the pharmaceutical composition disclosed herein, the content of active ingredient may vary depending on the disease severity. Preferably, the total daily dose of the peptide disclosed herein may be approximately 0.0001 μg to 500 mg per 1 kg of body weight of a patient. However, the effective dose of the peptide is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition disclosed herein. The pharmaceutical composition disclosed herein is not particularly limited to the formulation, and administration route and mode, as long as it shows suitable effects.

The pharmaceutical composition disclosed herein is expected to have longer in-vivo duration of efficacy and titer, thereby remarkably reducing the number and frequency of administration thereof.

Moreover, the pharmaceutical composition may be administered alone or in combination or coincident with other pharmaceutical formulations showing prophylactic or therapeutic efficacy.

In still another aspect, the present specification provides a method for preventing or treating of cancer, proliferative retinopathies, AMD and RA and related diseases comprising the step of administering to a subject the chimeric protein or the pharmaceutical composition including the same.

As used herein, the term "prevention" means all of the actions by which the occurrence of the disease is restrained or retarded.

As used herein, the term "treatment" means all of the actions by which the symptoms of the disease have been alleviated, improved or ameliorated. In the present specification, "treatment" means that the symptoms cancer, proliferative retinopathy, AMD or RA are alleviated, improved or ameliorated by administration of the fusion proteins disclosed herein.

As used herein, the term "administration" means introduction of an amount of a predetermined substance into a patient by a certain suitable method. The composition disclosed herein may be administered via any of the common routes, as long as it is able to reach a desired tissue, for example, but is not limited to, intraperitoneal, intravenous, intramuscular, subcutaneous, intradermal, oral, topical, intranasal, intrapulmonary, or intrarectal administration. However, since peptides are digested upon oral administration, active ingredients of a composition for oral administration should be coated or formulated for protection against degradation in the stomach.

In the present specification, the term "subject" is those suspected of having cancer, proliferative retinopathies, AMD or RA. However, any subject to be treated with the fusion proteins or the pharmaceutical composition disclosed herein is included without limitation. The pharmaceutical composition including the fusion peptide disclosed herein is administered to a subject suspected of having cancer, proliferative retinopathies, AMD or RA.

The therapeutic method of the present specification may include the step of administering the composition including the fusion protein at a pharmaceutically effective amount. The total daily dose should be determined through appropriate medical judgment by a physician, and administered once or several times. The specific therapeutically effective dose level for any particular patient may vary depending on various factors well known in the medical art, including the kind and degree of the response to be achieved, concrete compositions according to whether other agents are used therewith or not, the patient's age, body weight, health condition, gender, and diet, the time and route of administration, the secretion rate of the composition, the time period of therapy, other drugs used in combination or coincident with the composition disclosed herein, and like factors well known in the medical arts.

In still another aspect, the present specification provides a use of the therapeutic protein or the pharmaceutical composition including the same in the preparation of drugs for the prevention or treatment of cancer, proliferative retinopathies, AMD or RA and related diseases.

In one embodiment, the dose of the composition may be administered daily, semi-weekly, weekly, bi-weekly, or monthly. The period of treatment may be for a week, two weeks, a month, two months, four months, six months, eight months, a year, or longer. The initial dose may be larger than a sustaining dose. In one embodiment, the dose ranges from a weekly dose of at least 0.01 mg, at least 0.25 mg, at least 0.3 mg, at least 0.5 mg, at least 0.75 mg, at least 1 mg, at least 1.25 mg, at least 1.5 mg, at least 2 mg, at least 2.5 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 50 mg, at least 55 mg, at least 60 mg, at least 65 mg, or at least 70 mg. In one embodiment, a weekly dose may be at most 0.5 mg, at most 0.75 mg, at most 1 mg, at most 1.25 mg, at most 1.5 mg, at most 2 mg, at most 2.5 mg, at most 3 mg, at most 4 mg, at most 5 mg, at most 6 mg, at most 7 mg, at most 8 mg, at most 9 mg, at most 10 mg, at most 15 mg, at most 20 mg, at most 25 mg, at most 30 mg, at most 35 mg, at most 40 mg, at most 50 mg, at most 55 mg, at most 60 mg, at most 65 mg, or at most 70 mg. In a particular aspect, the weekly dose may range from 0.25 mg to 2.0 mg, from 0.5 mg to 1.75 mg. In an alternative aspect, the weekly dose may range from 10 mg to 70 mg.

EXAMPLES

Example 1—Production of the Chimeric Molecule Comprising VEGF Antibody and Ang2 Binding Peptide in HEK293 Cells Chimeric molecules named AMD A, B, C, D and E (see Table 1) were expressed through transient expression by HEK-293 cells. Briefly, DNAs (SEQ ID NOS: 20, 21, 22 and 25) for the fusion proteins comprising VEGF antibody light chain with or without Ang2 binding peptides and DNAs (SEQ ID NOS: 19, 23 and 24) for the fusion proteins comprising VEGF antibody heavy chain with Ang2 binding peptides were synthesized and cloned into expression vectors. The complete expression constructs comprising the genes were confirmed by DNA sequencing. DNA constructs were transformed into *E. coli* DH5alfa competent cells (Invitrogen). Single clone was selected and cultured in LB broth with antibiotics (kanamycin, 25 ug/mL). DNA plasmids were extracted with Qiagen Plasmid Maxi Kit (Qiagen) following manufacture's protocol. Plasmid concentration was measured by NanoDrop (Thermo Fisher). The expression plasmid constructs containing the DNA sequences encoding the genes of interest, were introduced into HEK-293 cells transiently by using polyethylenimine (PEI). The transfected cells were treated by alproic acid (VPA) 24 hours post transfection to enhance protein expression.

TABLE 1

AMD Molecules

|  | AMD-A | AMD-B | AMD-C | AMD-D | AMD-E |
|---|---|---|---|---|---|
| Light Chain | Peptide L1-15 (No LE*) fused to N-terminus of Bevacizumab light chain | Bevacizumab light chain | Peptide L1-15 (with LE) fused to N-terminus of Bevacizumab light chain | Bevacizumab light chain | Bevacizumab light chain |
| Light Chain DNA SEQ ID NO | SEQ ID NO: 21 (LY2.55.1) | SEQ ID NO: 25 (LY2.55.5) | SEQ ID NO: 22 (LY2.55.2) | SEQ ID NO: 25 (LY2.55.5) | SEQ ID NO: 20 (DHAMDL083016) |
| Heavy Chain | Peptide L1-15 (No LE) fused to N-terminus of Bevacizumab heavy chain | Peptide L1-15 (No LE) fused to N-terminus of Bevacizumab heavy chain | Peptide L1-15 (with LE) fused to N-terminus of Bevacizumab heavy chain | Peptide L1-15 (with LE) fused to N-terminus of Bevacizumab heavy chain | Peptide 2xCon4(C) fused to the C-terminus of the Heavy Chain of Bevacizumab |
| Heavy Chain DNA SEQ ID NO | SEQ ID NO: 23 (LY2.55.3) | SEQ ID NO: 23 (LY2.55.3) | SEQ ID NO: 24 (LY2.55.4) | SEQ ID NO: 24 (LY2.55.4) | SEQ ID NO: 19 (DHAMDH02083016) |

*LE is one of the flanking sequences, which were present both in the original phage clone when the peptides were screened and in the subsequent peptibody (Peptide-Fc fusion) molecules.

After approximately 6 days of culturing, the cell culture media were harvested by clarifying centrifugation at 9000 rpm for 30-60 minutes followed by filtration through 0.22 micrometer filters. The clarified supernants were loaded to a Protein A affinity column and the chimeric molecules (AMD-A, B, C, D and E) were purified. The chimeric molecules were eluted using 2 M arginine solution, pH 4 from the protein A column. FIG. 1 shows a representative chromatograph of the Protein A column step. Table 2 summarizes the results from the purification of the chimeric molecules. As shown in Table 2, chimeric molecules containing a total of 2 copies L1-15 peptides (AMD-B and AMD-D), both fused to the N-terminals of the heavy chain, had significantly higher expression levels comparing to the ones with a total of four copies of L1-15 peptides (AMD-A and AMD-C), wherein there is one each of L1-15 peptide fused to the N-terminals of both the light chains and the heavy chains of the antibody. With or without the flanking sequence LE as part of the L1-15 peptide did not appear to affect the expression of the chimeric molecules.

The expression level of AMD-E was comparable to that of AMD-B and AMD-D (Table 2). AMD-E has one Peptide 2xCon4(C) fused to each of the C-terminus of the heavy chains of Bevacizumab. The purity of the products were analyzed using SDS electrophoresis and/or HPLC methods.

TABLE 2

Summary of Protein A Affinity Chromatography Purification

|  | AMD-A | AMD-B | AMD-C | AMD-D | AMD-E |
|---|---|---|---|---|---|
| Approximate culture volume (ml) | 150 | 200 | 150 | 150 | 200 |
| Protein A Pool Volume (ml) | 3 | 9 | 5 | 12 | 17 |
| OD280 | 0.24 | 1.14 | 0.29 | 0.88 | 0.80 |
| Approximate amount in the Protein A Pool, (mg) | 0.45 | 6.4 | 0.91 | 6.6 | 8.5 |

Example 2—Production of the Chimeric Molecule Comprising VEGF Trap and Ang2 Binding Peptide in CHO Cells DNA for the chimeric molecule comprising the VEGF Receptor-Fc fusion protein (VEGF Trap) and the Ang2 binding peptide (SEQ ID NO:6, named as ASKB-E06) is synthesized and cloned into an expression vector. The complete expression construct comprising the DNA gene is confirmed by DNA sequencing. The expression construct is amplified by transforming into DH10B *E. coli* and culturing the cells overnight. DNA for the expression construct was prepared and purified by endo-free plasmid kit (from QIAGEN®).

Cell lines stably expressing ASKB-E06 is obtained by transfecting the expression construct into $GS^{-/-}$ Chinese hamster ovarian cells (CHO) by electroporation and screening for transfected CHO cells using a selective culture medium without glutamine (EX-CELL® CD CHO Fusion Growth Medium). In this manner 32 or more stable mini-pools are established and the leading mini-pool is selected based on expression level in batch and fed-batch cultures. The expression levels are detected by ELISA titer assay. Single cloning is performed by limited dilution and using clone media, two leading single clones out of more than 100 positive clones are selected based on productivity and cell growth in batch and fed-batch culture. The lead clones are expanded and seeded at $0.5 \times 10^6$ cells/mL, total 300 mL in 2 L shake flasks, and the cells are cultured at 37° C., 5% $CO_2$, 70% HMR conditions and shaking at 120 rpm. The cultures are fed by using 5% Acti CHO® Feed A+0.5% Feed B (from GE Health) on Day 3, 6, 7, 8 and 9. The cell viability, viable cell density are monitored every other day, the cultures are harvested on Day 11-13.

The cell culture medium is harvested by clarifying approximately 600 mL of the cultured cell medium through centrifugation at 2000 rpm for 10 minutes followed by filtration. The clarified supernatant is loaded to a Protein A affinity column and the chimeric molecule is purified. The protein is further purified using ion exchange chromatography, hydrophobic interaction chromatography, hydroxyapatite chromatography, and/or mixed mode chromatography. The product is further concentrated and buffer exchanged using UFDF and further formulated. The purity of the product is analyzed using CE-SDS and HPLC methods.

Figure 2:
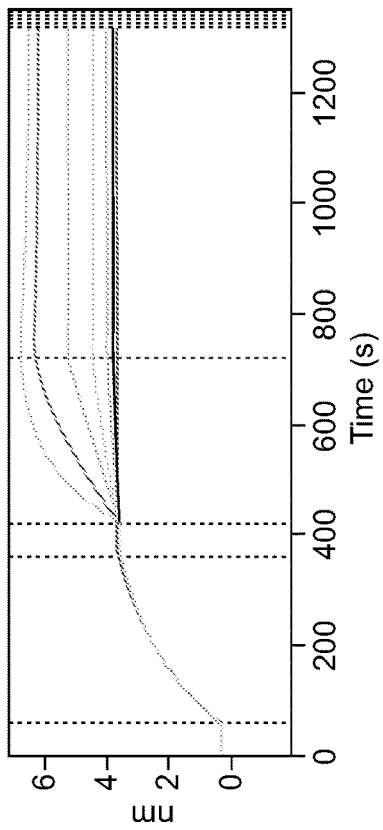
FIG. 2. Kinetics of Ang-1 or Ang-2 Binding to AMD-E As Analyzed by Octet Red96.
Figure 2:
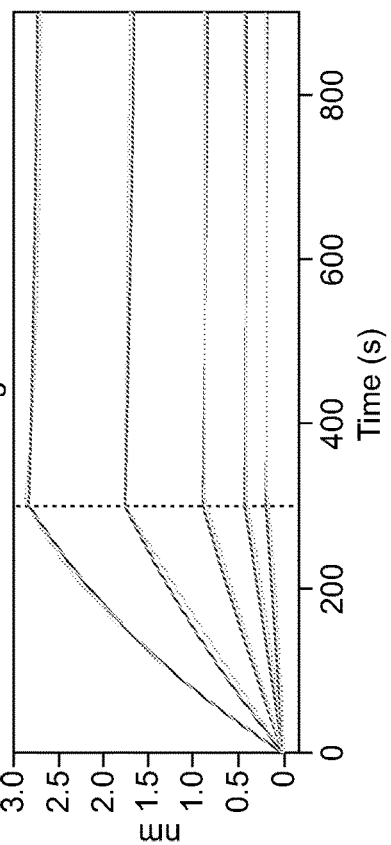
Figure 2:
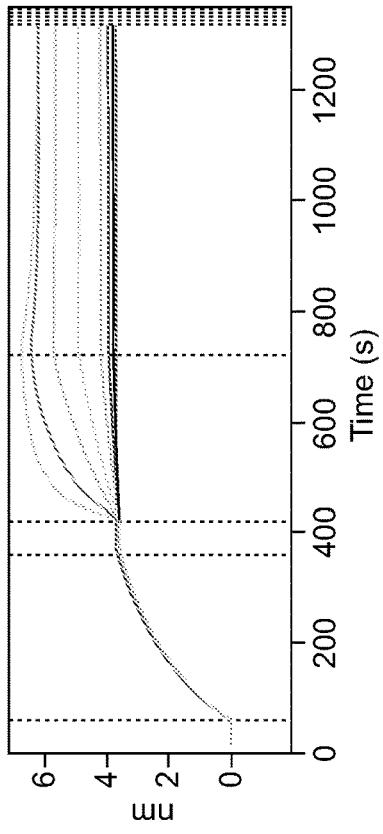
Figure 2:
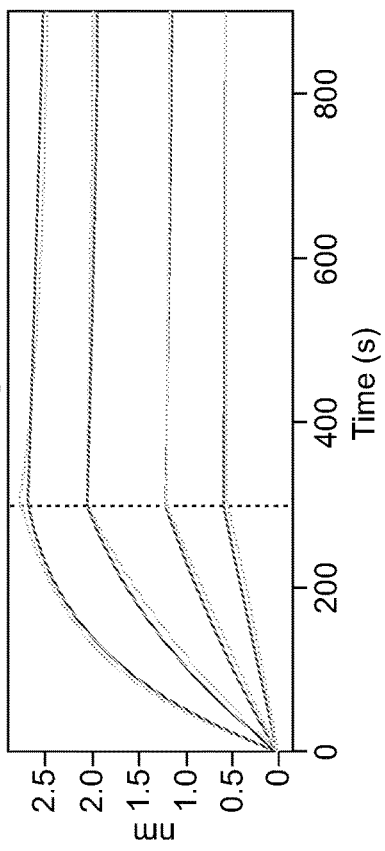

Example 3—Molecular Assays to Evaluate Dual Antagonist Activities of the Chimeric Molecules Molecular assays (Octet Binding Affinity, Affinity ELISA, and Blocking ELISA) were developed to assess direct binding of the chimeric molecules to ANG-1, Ang-2 and/or VEGF, and the effect of the chimeric molecules on the Ang1:Tie-2 interaction, Ang-2:Tie-2 interaction and/or VEGF:VEGF receptor interaction. These in vitro assays are described as the following:

Octet Affinity: Purified recombinant human VEGF protein was ordered from Life-Technologies (Cat. #PHC9391). Human Ang1 or Ang2 protein were ordered from R&D System. Analysis was carried out using Octet Red96 from Pall ForteBio. Using anti-human IgG Fc sensors, a sample of chimeric molecule AMD-B, AMD-D, AMD-E or the control antibody Bevacizumab was loaded for 300 seconds at 3 ug/mL in the kinetics buffer. Ligands ANG1, ANG2, or VEGF samples were associated for 300 seconds using a dilution series starting at 5 or 10 ug/mL and sequentially diluting 2-fold for 7 wells. Dissociation was run for 600 seconds. Data was analyzed using a 1:1 model with global fit. A representative binding kinetics graph is shown in FIG. 2. The binding affinity results are summarized in Tables 3A, 3B and 3C. The results showed that the chimeric molecules AMD-B, AMD-D, and AMD-E were able to bind to Ang1, Ang2, and VEGF. It was also noticed that the chimeric molecule AMD-B with four L1-15 peptides fused to the N-terminals of the antibody had reduced affinity to VEGF when comparing to the control antibody Bevacizumab. AMD-D and AMD-E showed comparable affinity to VEGF comparing to the control antibody ASKB1202, a biosimilar m An internal control, ASKB 1202, a biosimilar to Bevacizumab developed in-house.

TABLE 3A

Summary of the Octet Affinity analysis results - Binding of ANG-1.

| | kon (1/Ms) | koff (1/s) | KD (M) |
| --- | --- | --- | --- |
| AMD-B | 1.56E+05 | 2.69E−04 | 1.73E−09 |
| AMD-D | 1.75E+05 | 2.41E−04 | 1.37E−09 |
| AMD-E | 9.42E+04 | 1.01E−04 | 1.07E−09 |

TABLE 3B

Summary of the Octet Affinity analysis results - Binding of ANG-2.

| | kon (1/Ms) | koff (1/s) | KD (M) |
| --- | --- | --- | --- |
| AMD-B | 3.34E+04 | 4.33E−05 | 1.30E−09 |
| AMD-D | 3.68E+04 | 2.39E−05 | 6.49E−10 |
| AMD-E | 3.54E+04 | 5.52E−05 | 1.56E−09 |

TABLE 3C

Summary of the Octet Affinity analysis results - Binding of VEGF.

| | kon (1/Ms) | koff (1/s) | KD (M) |
| --- | --- | --- | --- |
| Bevacizumab | 8.03E+04 | <1.0E−07 | <1.0E−12 |
| AMD-B | 1.41E+05 | 3.42E−05 | 2.42E−10 |
| AMD-D | 1.01E+05 | <1.0E−07 | <1.0E−12 |
| AMD-E | 1.38E+05 | <1.0E−07 | <1.0E−12 |

Affinity ELISA: Purified recombinant human VEGF protein was ordered from Life-Technologies (Cat. #PHC9391). VEGF is reconstituted in BSA solution at 0.1 mg/mL as recommended by the manufacturer. Aliquots the samples were made and stored at −20° C.

Using microtiter plates, approximately 100 microliters per well of VEGF is added to each well and the plates were incubated about 2 hours, after which the plates are washed with phosphate buffered saline (PBS) containing about 0.1 percent Tween-20 four times. The wells are then blocked using about 250 microliters per well of about 5 percent BSA in PBS, and the plates were incubated at room temperature for about 2 hours. After incubation, excess blocking solution is discarded, and about 100 microliters of AMD-A, B, C, D or E was added to a well in a dilution series starting at a concentration of about 40 nanomolar and then serially diluting 4-fold in PBS containing about 1 percent BSA. The plates were then incubated overnight at room temperature. After incubation, plates were washed with PBS containing about 0.1 percent Tween-20. Washing was repeated four additional times, after which about 100 microliters per well of goat anti-human IgG(Fc)-HRP (Pierce Chemical Co., catalog #31416) previously diluted 1:5000 in PBS containing 1 percent BSA was added. Plates were incubated approximately 1 hour at room temperature. Plates were then washed five times in PBS containing about 0.1 percent Tween-20, after which about 100 microliters per well of TMB (3,3',5,5'-Tetramethylbenzidine Liquid Substrate System; Sigma Chemical Company, St. Louis, Mo., catalog number T8665) substrate was added and plates are incubated about 5-15 minutes until blue color developed. Absorbance was then read in a spectrophotometer at about 450 nm.

Figure 3:
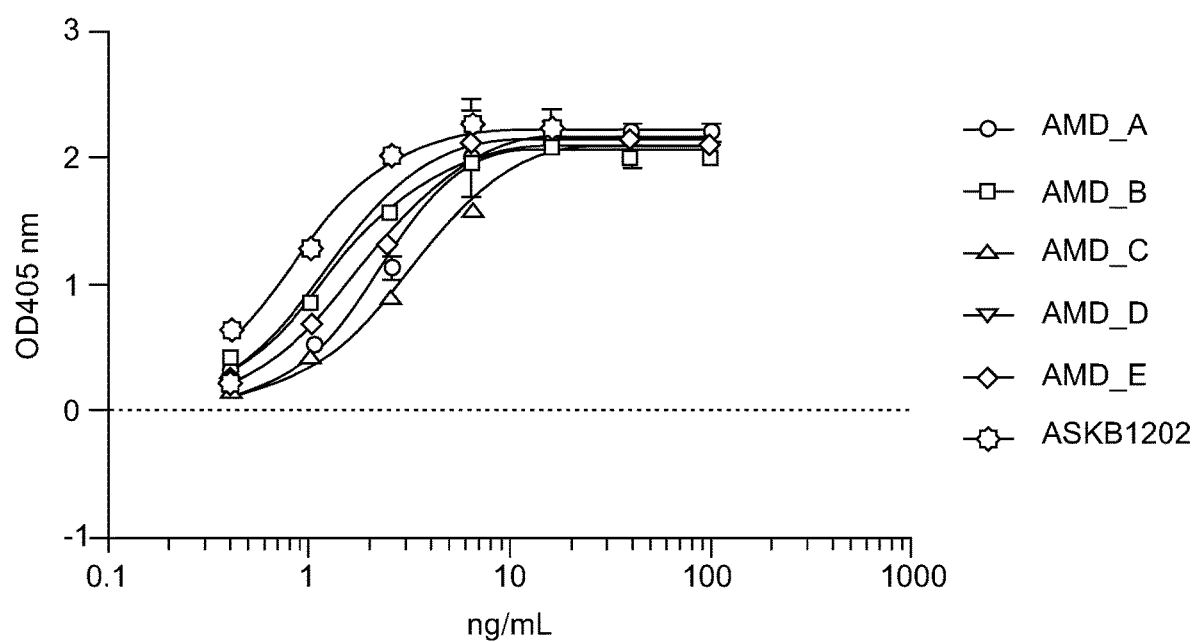
FIG. 3. Blocking of Binding of Ang-1 and Ang-2 to Tie-2 by AMD-E.

FIG. 3 shows the ELISA results of binding of VEGF to AMD-A, B, C, D, and E. An internal control, ASKB 1202, a biosimilar to Bevacizumab currently in development, was used as a positive control. The results showed that all the molecules AMD-A, B, C, D and E retained abilities to bind to VEGF. The EC-50 results are summarized in Table 4. The results showed that the AMD-B and AMD-D had VEGF binding affinity close to ASKB1202. In addition, AMD-B and AMD-D had stronger VEGF binding affinity than AMD-A and AMD-C.

TABLE 4

Affinity ELISA Results: Binding of VEGF to AMD-A, B, C, D and E.

| | EC-50 (ng/ml) |
| --- | --- |
| AMD-A | 2.296 |
| AMD-B | 1.278 |
| AMD-C | 3.328 |
| AMD-D | 1.247 |
| AMD-E | 1.87 |
| ASKB1202 | 0.8002 |

Blocking ELISA: The chimeric molecules were assessed in their abilities in blocking the binding of Ang1 and Ang2 to their receptor Tie-2. 96 well microtiter plate (Nunk) was coated with 100 uL final concentration 100 ng/mL of human Tie2-Fc (R&D System, 313-T1) diluted in 0.1 M carbonate (pH9.3) at 4° C. overnight. The plate was then blocked for 2 hours with 5% BSA in PBST (0.05% Tween 20). Purified chimeric molecule, at starting concentration of 1000 ng/mL, was serially diluted with dilution factor of three in PBS with 1% BSA. Human Ang1 or Ang2 protein (R&D System) was added to final concentration of 50 ng/mL and incubated at room temperature for 1 hour. The Chimeric molecule-Ang1 or Chimeric molecule-Ang2 mixture was then added into microtiter plate coated with human Tie2-Fc and incubate for another 1 hour at room temperature. 100 uL anti-Ang1 or anti-Ang2 monoclonal antibody (R&D System) was added into each well at final concentration of 1 ug/mL and incubated for 1 hour at room temperature. Horseradish-peroxidase (HRP) conjugated anti-mouse IgG secondary antibody was added at 1:5000 dilution and incubated for 1 hour at room temperature. Standard colorimetric response was developed by using TMB (Pierce). Absorbance was read at OD450 by spectrophotometer. Between each step, the plate was washed 5 time with 100 uL PBS.

Figure 4A:
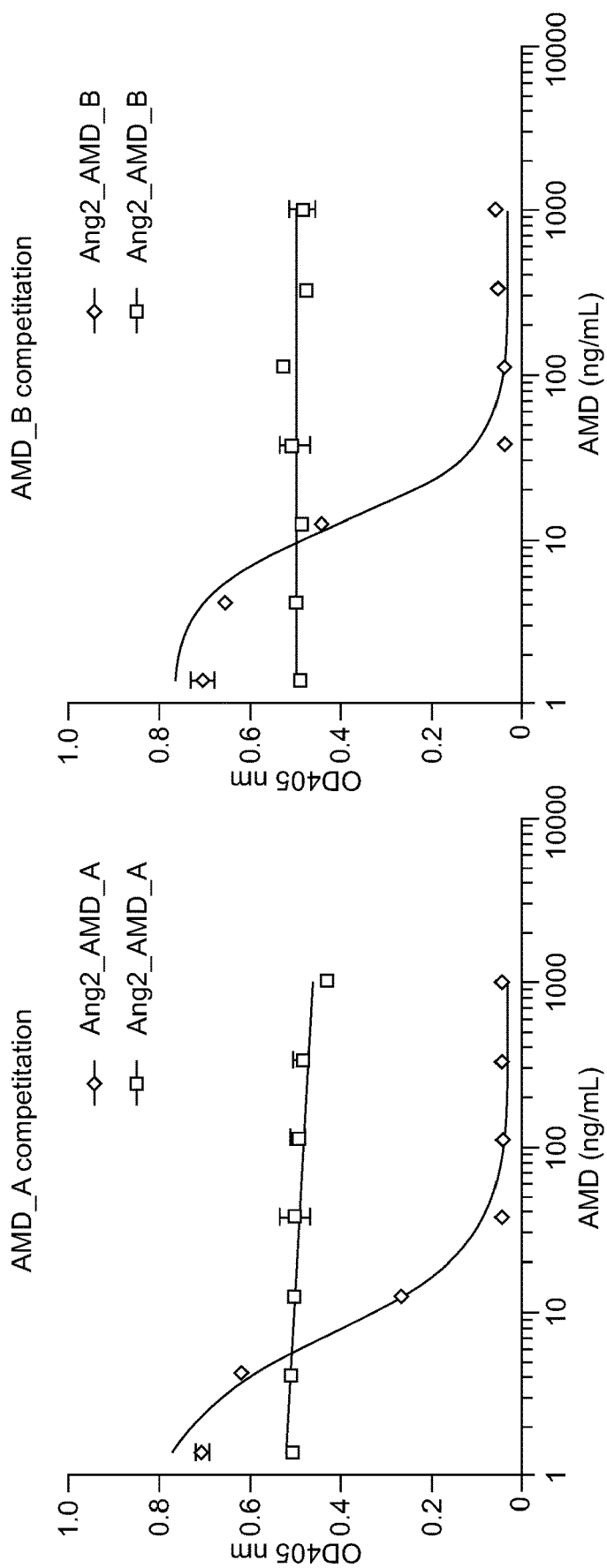
FIG. 4A. Blocking of Binding of Ang-1 and Ang-2 to Tie-2 by AMD-A and AMD-B.
Figure 4B:
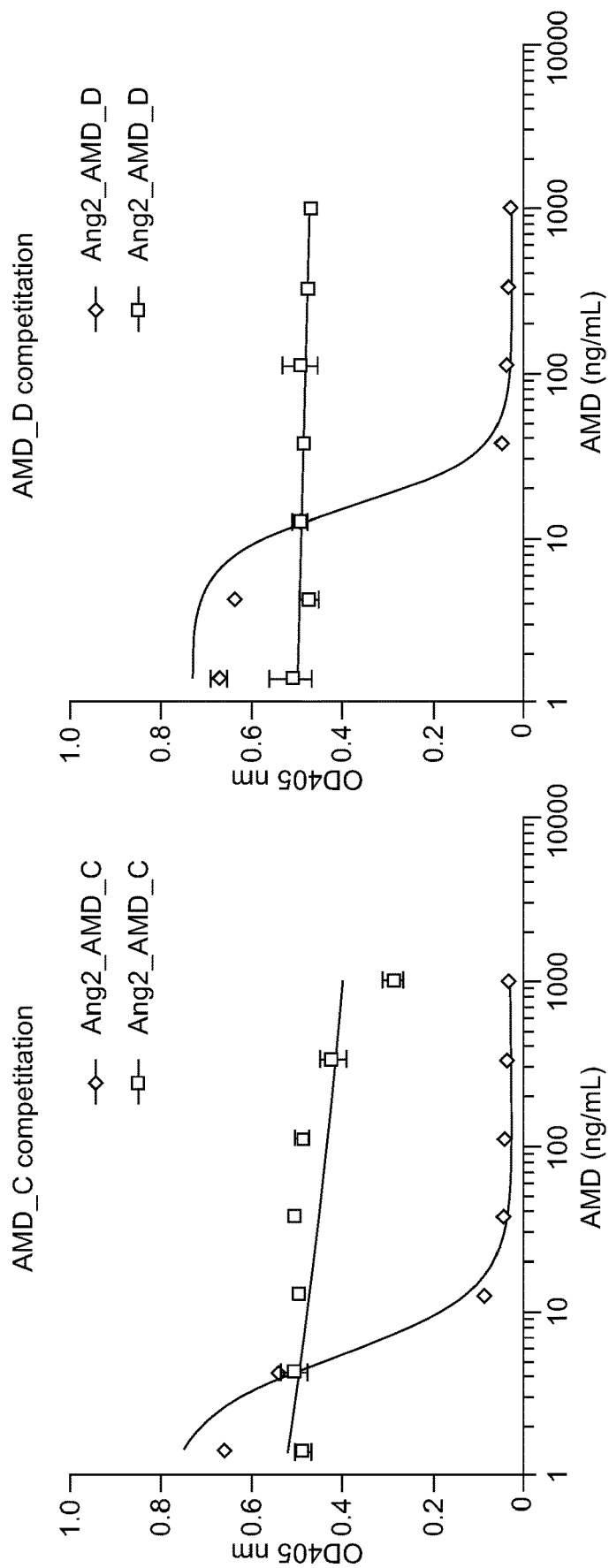
FIG. 4B. Blocking of Binding of Ang-1 and Ang-2 to Tie-2 by AMD-C and AMD-D.

The dose dependent inhibition or lack of inhibition of the binding of Ang1 and Ang-2 to receptor Tie-2 are shown in FIG. 4. The IC-50 results are summarized in Table 5. The results showed that the chimeric molecules AMD-A, B, C, and D selectively inhibited the binding of Ang2 to Tie-2, with IC-50 in the range of 5-15 ng/ml; while their abilities in inhibiting the binding of Ang-1 to Tie-2 were very weak, if any, despite the fact that they all were able to bind to Ang1. The results also showed that AMD-A and AMD-C, both comprising 4 copies of the peptide L1-15 had lower IC-50 than AMD-B and AMD-D. AMD-E was able to inhibit the association of both Ang-1 and Ang-2 to their receptor Tie-2.

TABLE 5

Blocking ELISA Results: Inhibition of
Binding of Ang-1 or Ang-2 to Tie-2.

|  | IC-50 of inhibiting Ang-1 Binding (ng/ml) | IC-50 of Inhibiting Ang-2 Binding (ng/ml) |
|---|---|---|
| AMD-A | Not detected | 7.3 |
| AMD-B | Not detected | 12.49 |
| AMD-C | Not detected | 5.136 |
| AMD-D | Not detected | 15.21 |
| AMD-E | 10 (estimated) | 2.107 |

Example 4—Cell-Based Activity Assay: In Vitro Human Umbilical Vein Endothelial Cells (HUVEC) Tube-Formation Assay In order to confirm whether or not ASKB-E06 inhibits angiogenesis, proliferation, migration, and differentiation assays of human umbilical vein endothelial cells (HUVEC) are performed.

(1) Proliferation Inhibition of HUVEC by ASKB-E06

After 10,000 HUVEC were added to 100 μl of EBM-2 medium (Lonza, Switzerland), EBM-2 medium having VEGF-A (50 ng/ml) is added thereto, or EBM-2 medium including VEGF-A (50 ng/ml) and ASKB-E06 sample at different concentration is added thereto in each well of a 96-well plate, followed by incubation under 5% $CO_2$, at 37° C. for 72 hours. Then, 10 μl of WST-1 solution was added thereto, followed by incubation at 37° C. for 4 hours. Absorbance is measured at 410 nm with a reference of 610 nm.

(2) Migration Inhibition of HUVEC by ASKB-E06

After a bottom of Transwells, (Corning Inc., US) having a pore size of 8-μm is coated with 0.1% gelatin and mounted in a 24-well plate, a lower chamber is filled with 600 μl of EBM-2 medium (Lonza), EBM-2 with VEGF-A (50 ng/ml), or EBM-2 with VEGF-A (50 ng/ml) and ASKB-E06 sample at different concentration. An upper chamber is provided with 100 μl of EBM-2 medium containing $1\times10^5$ HUVEC. After incubation in 37° C. cell incubator for 4 hours, a filter is detached from the Transwell and cells are fixed with methanol for 1 minute and stained with Hematoxylin/Eosin. Cells which do not migrate but are left on an upper surface of the transwell are completely removed with a cotton swab. Five random fields among the cells migrated through the filter are arbitrarily chosen under an optical microscope (×100) and the number thereof is counted.

(3) Inhibition of Tube Formation by ASKB-E06

In order to confirm that ASKB-E06 can inhibit differentiation of HUVEC, tube formation assay is performed. More specifically, after a 96-well plate is coated with Growth Factor Reduced Matrigel (BD Biosciences, US), 15,000 HUVEC in 100 μl of EBM-2 medium, EBM-2 medium with VEGF-A (50 ng/ml), or EBM-2 medium with VEGF-A (50 ng/ml) and an antibody sample are added to each well, followed by incubation in 37° C. cell incubator for 6 hours. Then, tube formation is observed by using an inverted microscope.

Example 5—In Vivo Anti-Tumor Activity Study: Therapeutic Efficacy Studies with Systemically Administered Dual Antagonist Chimeric Molecules The chimeric molecule ASKB-E06 is administered subcutaneously to A431 tumor-bearing mice at a once-per-day schedule 72 hours after tumor challenge. The doses used are 1000, 200, 40 and 8 ug/mouse/day. A total of 20 doses is given to all animals. Tumor volumes and body weights are recorded three times/week. At the end of the study, animals are sacrificed, and their sera are collected for measuring ASKB-E06 levels by ELISA. Tumors and a panel of normal tissues are collected from all groups.

The following non-limiting examples are provided for illustrative purposes only in order to facilitate a more complete understanding of the disclosed subject matter. These examples should not be construed to limit any of the embodiments described in the present specification, including those pertaining to the fusion peptides, pharmaceutical compositions, or methods and uses for treating cancer, proliferative retinopathies, AMD or RA.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

SEQUENCES

```
SEQ ID NO: 1, 2xCon4(C) (Ang2 peptide)
(1)         10         20         30         40         50
       GGGGGAQQEE CEWDPWTCEH MGSGSATGGS GSTASSGSGS ATHQEECEWD PWTCEHMLE SEQ ID NO: 2, Bevacizumab Heavy Chain
(1)         10         20         30         40         50         60
       EVQLVESGGG LVQPGGSLRL SCAASGYTFT NYGMNWVRQA PGKGLEWVGW INTYTGEPTY 70         80         90        100        110        120
       AADFKRRFTF SLDTSKSTAY LQMNSLRAED TAVYYCAKYP HYYGSSHWYF DVWGQGTLVT 130        140        150        160        170        180
       VSSASTKGPS VFPLAPSSKS TSGGTAALGC LVKDYFPEPV TVSWNSGALT SGVHTFPAVL 190        200        210        220        230        240
       QSSGLYSLSS VVTVPSSSLG TQTYICNVNH KPSNTKVDKK VEPKSCDKTH TCPPCPAPEL 250        260        270        280        290        300
       LGGPSVFLFP PKPKDTLMTS RTPEVTCVVV DVSHEDPEVK FNWYVDGVEV HNAKTKPREE 310        320        330        340        350        360
       QYNSTYRVVS VLTVLHQDWL NGKEYKCKVS NKALPAPIEK TISKAKGQPR EPQVYTLPPS 370        380        390        400        410        420
       REEMTNKQVS LTCLVKGEYP SDIAVEWESN GQPENNYKTT PPVLDSDGSF FLYSKLTVDK 430        440        450
       SRWQQGNVFS CSVMHEALHN HYTQKSLSLS PGK SEQ ID NO: 3 Bevacizumab Light Chain
(1)         10         20         30         40         50         60
       DIQMTQSPSS LSASVGDRVT ITCSASQDIS NYLNWYQQKP GKAPKVLIYF TSSLHSGVPS 70         80         90        100        110        120
       RFSGSGSGTD FTLTISSLQP EDFATYYCQQ YSTVPWTFGQ GTKVEIKPTV AAPSVFIFPP 130        140        150        160        170        180
       SDEQLKSGTA SVVCLLNNFY PREAKVQWKV DNALQSGNSQ ESVTEQDSKD STYSLSSTLT 190        200        210
       LSKADYEKHK VYACEVTHQG LSSPVTKSFN RGEC SEQ ID NO: 4, 2xCon4(C) fused to the C-terminus of the Heavy Chain
of Bevacizumab
(1)         10         20         30         40         50         60
       EVQLVESGGG LVQPGGSLPL SCAASGYTFT NYGMNWVRQA PGKGLEWVGW INTYTGEPTY 70         80         90        100        110        120
       AADFKRRFTF SLDTSKSTAY LQMNSLRAED TAVYYCAKYP HYYGSSHWYF DVWGQGTLVT 130        140        150        160        170        180
       VSSASTKGPS VFPLAPSSKS TSGGTAALGC LVKDYFPEPV TVSWNSGALT SGVHTFPAVL 190        200        210        220        230        240
       QSSGLYSLSS VVTVPSSSLG TQTYICNVNH KPSNTKVDKK VEPKSCDKTH TCPPCPAPEL 250        260        270        280        290        300
       LGGPSVFLFP PKPKDTLMIS RTPEVTCVVV DVSHEDPEVK FNWYVDGVEV HNAKTKPREE 310        320        330        340        350        360
       QYNSTYRVVS VLTVLHQDWL NGKEYKCKVS NKALPAPIEK TISKAKGQPR EPQVYTLPPS 370        380        390        400        410        420
       REEMTKNQVS LTCLVKGFYP SDIAVEWESN GQPENNYKTT PPVLDSDGSF FLYSKLTVDK
```

```
                    430        440        450        460        470        480
               SPWQQGNVFS CSVMHEALHN HYTQKSLSLS PGKGGGGGAQ QEECEWDPWT CEHMGSGSAT 490        500        510
               GGSGSTASSG SGSATHQEEC EWDPWTCEHM LE

SEQ ID NO: 5, VEGF Trap Aflibercept
(1)             10         20         30         40         50         60
               SDTGRPFVEM YSEIPEIIHM TEGRELVIPC RVTSPNITVT LKKFPLDTLI PDGKRIIWDS 70         80         90        100        110        120
               RKGFIISNAT YKEIGLLTCE ATVNGHLYKT NYLTHPQTNT IIDVVLSPSH GIELSVGEKL 130        140        150        160        170        180
               VLNCTARTEL NVGIDFNWEY PSSKHQHKKL VNRDLKTQSG SEMKKFLSTL TIDGVTRSDQ 190        200        210        220        230        240
               GLYTCAASSG LMTKKNSTFV RVHEKDKTHT CPPCPAPELL GGPSVFLFPP KPKDTLMISP 250        260        270        280        290        300
               TPEVTCVVVD VSHEDPEVKF NWYVDGVEVK NAKTKPREEQ YNSTYRVVSV LTVLHQDWLN 310        320        330        340        350        360
               GKEYKCKVSN KALPAPIEKT ISKAKGQPRE PQVYTLPPSR DELTKNQVSL TCLVKGFYPS 370        380        390        400        410        420
               DIAVEWESNG QPENNYKTTP PVLDSDGSFF LYSKLTVDKS RWQQGNVFSC SVMHEALHNH

430
               YTQKSLSLSP G(K)

SEQ ID NO: 6, 2xCon4(C) fused to the C-terminus of the VEGF Trap
(1)             10         20         30         40         50         60
               SDTGRPFVEM YSEIPEIIHM TEGRELVIPC RVTSPNITVT LKKFPLDTLI PDGKRIIWDS 70         80         90        100        110        120
               PKGFIISNAT YKEIGLLTCE ATVNGHLYKT NYLTHPQTNT IIDVVLSPSH GIELSVGEKL 130        140        150        160        170        180
               VLNCTARTEL NVGIDFNWEY PSSKHQHKKL VNRDLKTQSG SEMKKFLSTL TIDGVTRSDQ 190        200        210        220        230        240
               GLYTCAASSG LMTKKNSTFV RVHEKDKTHT CPPCPAPELL GGPSVFLFPP KPKDTLMISR 250        260        270        280        290        300
               TPEVTCVVVD VSHEDPEVKF NWYVDGVEVH NAKTKPREEQ YNSTYRVVSV LTVLHQDWLN 310        320        330        340        350        360
               GKEYKCKVSN KALPAPIEKT ISKAKGQPRE PQVYTLPPSR DELTKNQVSL TCLVKGFYPS 370        380        390        400        410        420
               DIAVEWESNG QPENNYKTTP PVLDSDGSFF LYSKLTVDKS PWQQGNVFSC SVMHEALHNH 430        440        450        460        470        480
               YTQKSLSLSP GKGGGGGAQQ EECEWDPWTC EHMGSGSATG GSGSTASSGS GSATHQEECE

490
               WDPWTCEHML E

SEQ ID NO: 7, L1-7
AQQTNFMPM DDLEQRLYEQ FILQQG

SEQ ID NO: 8, L1-10
AQQKFQPLD ELEQTLYEQF MLQQA

SEQ ID NO: 9, L1-15
AQQKYQPLD ELDKTLYDQF MLQQG

SEC) ID NO: 10, L1-78
QTNFMPM DDLEQRLYEQ FILQQG

SEQ ID NO: 11, L1-10B
QKFQPLD ELEQTLYEQF MLQQA
```

-continued

| SEQUENCES |
|---|

SEQ ID NO: 12, L1-15B
QKYQPLD ELDKTLYDQF MLQQG

SEQ ID NO: 13, Linker
(GGGGS)n
wherein n = 0-4

SEQ ID NO: 14, L1-15/Light Chain Fusion molecule
AQQKYQPLDELDKTLYDQFMLQQGGGGGSGGGGSGGGGSDIQMTQSPSSLSASVGDRVTITCSASQDISNYLNWYQQ
KPGKAPKVLIYFTSSLHSGVPSRFSGSGSGTDFTLTISSLQPEDFATYYCQQYSTVPWTFGQGTKVEIKRTVAAPSV
FIFPPSDEQLKSGTASVVCLLNNFYPREAKVQWKVDNALQSGNSQESVTEQDSKDSTYSLSSTLTLSKADYEKHKVY
ACEVTHQGLSSPVTKSFNRGEC SEQ ID NO: 15, L1-15 Heavy Chain Fusion Molecule
AQQKYQPLDELDKTLYDQFMLQQGGGGGSGGGGSGGGGSEVQLVESGGGLVQPGGSLRLSCAASGYTFTNYGMNWVR
QAPGKGLEWVGWINTYTGEPTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLTVDKSRW
QQGNVFSCSVMHEALHNHYTQKSLSLSPGK SEQ ID NO: 16, L1-15 with LE Heavy Chain Fusion Molecule
AQQKYQPLDELDKTLYDQFMLQQLEGGGGSGGGGSGGGGSEQQLVESGGGLVQPGGSLRLSCAASGYTFTNYGMNW
VRQAPGKGLEWVGWINTYTGEPTYAADFKRRFTFSLDTSKSTAYLQMNSLRAEDTAVYYCAKYPHYYGSSHWYFDVW
GQGTLVTVSSASTKGPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK SEQ ID NO: 17, 2xCon4(C) fused to the C-terminus of the Heavy Chain of
Bevacizumab, with linker peptide GGGGSGGGGSGGGGS
```
          10         20         30         40         50         60
EVQLVESGGG LVQPGGSLPL SCAASGYTFT NYGMNWVRQA PGKGLEWVGW INTYTGEPTY 70         80         90        100        110        120
AADFKRRFTF SLDTSKSTAY LQMNSLRAED TAVYYCAKYP HYYGSSHWYF DVWGQGTLVT 130        140        150        160        170        180
VSSASTKGPS VFPLAPSSKS TSGGTAALGC LVKDYFPEPV TVSWNSGALT SGVHYFPAVL 190        200        210        220        230        240
QSSGLYSLSS VVTVPSSSLG TQTYICNVNH KPSNTKVDKK VEPKSCDKTH TCPPCPAPEL 250        260        270        280        290        300
LGGPSVFLFP PKPKDTLMIS RTPEVTCVVV DVSHEDPEVK FNWYVDGVEV HNAKTKPREE 310        320        330        340        350        360
QYNSTYRVVS VLTVLHQDWL NGKEYKCKVS NKALPAPIEK TISKAKGQPR EPQVYTLPPS 370        380        390        400        410        420
REEMTKNQVS LTCLVKGFYP SDIAVEWESN GQPENNYKTT PPVLDSDGSF FLYSKLTVDK 430        440        450        460        470        480
SPWQQGNVFS CSVMHEALHN HYTQKSLSLS PGKGGGGAQ QEECEWDPWT CEHMGGGGSG 490        500
GGGSGGGGSA THQEECEWDPW TCEHMLE
```

SEQ ID NO: 18, L1-15 fused to the N-terminus of the VEGF Trap, with linker
peptide GGGGSGGGGSGGGGS
```
          10         20         30         40         50         60
AQQKYQPLDE LDKTLYDQFM LQQGGGGGSG GGGSGGGGSS DTGRPFVEMY SEIPEIIHMT 70         80         90        100        110        120
EGRELVIPCR VTSPNITVTL KKFPLDTLIP DGKRIIWDSR KGFIISNATY KEIGLLTCEA 130        140        150        160        170        180
TVNGHLYKTN YLTHRQTNTI IDVVLSPSHG IELSVGEKLV LNCTARTELN VGIDFNWEYP 190        200        210        220        230        240
SSKHQHKKLV NRDLKTQSGS EMKKFLSTLT IDGVTRSDQG LYTCAASSGL MTKKNSTFVR 250        260        270        280        290        300
VHEKDKTHTC PPCPAPELLS GPSVFLFPPK PKDTLMISRT PEVTCVVVDV SHEDPEVKFN
```

|     |     |     |     |     |     |
| --- | --- | --- | --- | --- | --- |
| 310 | 320 | 330 | 340 | 350 | 360 |
| WYVDGVEVHN | AKTKPREEQY | NSTYRVVSVL | TVLHQDWLNG | KEYKCKVSNK | ALPAPIEKTI |
| 370 | 380 | 390 | 400 | 410 | 420 |
| SKAKGQPREP | QVYTLPPSRD | ELTKNQVSLT | CLVKGFYPSD | LAVEWESNGQ | PENNYKTTPP |
| 430 | 440 | 450 | 460 | 470 |     |
| VLDSDGSFFL | YSKLTVDKSR | WQQGNVFSCS | VMHEALHNHY | TQKSLSLSPG | K |

SEQ ID NO: 19, DNA sequence (DHAMDH02083016) for 2xCon4(C) fused to the
C-terminus of the Heavy Chain of Bevacizumab, with linker peptide
GGGGSGGGGSGGGGS
ATGGGTTGGTCCTGTATCATTCTTTTCCTCGTCGCCACTGCCACCGGAGTCCACTCAGAAGTCCAGTTGGTGGAGTC
GGGAGGAGGACTGGTGCAGCCAGGCGGCTCCCTGCGCCTGTCCTGCGCGGCGTCCGGGTACACCTTCACCAACTACG
GCATGAACTGGGTCCGCCAGGCCCCCGGAAAGGGGCTGGAATGGGTCGGCTGGATCAACACTTACACCGGAGAACCT
ACCTACGCTGCCGATTTCAAGCGGCGCTTTACTTTCTCGCTGGACACCTCCAAGAGCACCGCCTATCTCCAAATGAA
CTCCCTGCGGGCCGAGGATACCGCCGTGTACTATTGCGCGAAGTACCCCACTATTACGGTTCGTCCCATTGGTACT
TCGACGTCTGGGGCCAGGGAACTCTTGTCACTGTGTCCTCCGCATCCACCAAGGGACCGTCAGTGTTCCCCCTGGCC
CCGTCCTCCAAAAGCACTAGCGGAGGAACCGCAGCCTTGGGATGCCTCGTCAAGGACTACTTTCCCGAGCCTGTCAC
CGTGTCGTGGAACTCCGGTGCCCTCACTTCGGGCGTGCACACGTTCCCAGCGGTGCTGCAGTCCAGCGGACTGTACT
CGCTGTCCTCCGTCGTGACCGTGCCCTTCATCGAGCCTGGGGACCCAGACCTACATTTGCAACGTGAACCACAAGCCC
TCCAACACCAAAGTGGACAAGAAGGTCGAACCAAAGAGCTGCGACAAGACCCACACTTGCCCGCCGTGCCCGGCCCC
TGAGTTGCTGGGTGGTCCATCGGTGTTCCTGTTCCCGCCTAAGCCGAAGGACACACTCATGATCAGCAGGACCCCCG
AAGTGACCTGTGTGGTGGTCGACGTGTCACATGAAGATCCCGAGGTCAAGTTCAATTGGTACGTGGACGGAGTGGAA
GTGCATAATGCCAAGACTAAGCCGAGAGAGGAACAGTACAACTCCACCTACCGGGTGGTGTCAGTGCTGACCGTGCT
CCATCAGGACTGGCTCAACGGGAAGGAGTACAAGTGCAAAGTGTCGAACAAGGCTCTCCCCGCCCCTATCGAGAAAA
CCATTAGCAAGGCTAAGGGACAGCCGCGGGAGCCGCAAGTGTACACCCTGCCCCCGAGCCGCGAAGAAATGACTAAG
AACCAAGTGTCCCTGACCTGTCTCGTGAAAGGGTTCTACCCGTCGGACATCGCTGTGGAGTGGGAGTCTAATGGTCA
ACCTGAGAACAACTACAAGACTACTCCCCCTGTGCTGGACTCCGATGGTTCCTTTTTCCTGTACTCAAAGCTGACCG
TGGACAAGTCCAGATGGCAGCAGGGCAACGTGTTCAGCTGCTCCGTGATGCATGAAGCACTTCACAACCACTACACC
CAGAAGTCCCTCAGCCTGTCTCCGGGGAAGGGCGGCGGAGGAGGGCCCAGCAGGAAGAGTGTGAATGGGACCCCTG
GACTTGTGAACACATGGGCGGCGGCTCCGGTGGAGGAGGATCCGGCGGAGGGGGCAGCGCGACGCACCAGGAGG
AGTGCGAATGGGATCCATGGACTTGCGAACACATGCTGGAGTGA SEQ ID NO: 20, DNA sequence (DHAMDL083016), for the light chain of
Bevacizumab
ATGGGTTGGTCCTGTATTATCCTCTTTTCTCGTCGCCACTGCCACCGGAGTGCACTCAGATATTCAGATGACCCAGAG
CCCCTCCTCACTGTCCGCTTCCGTGGGGGACCGCGTGACTATCACTTGCTCGGCTTCCCAAGATATCTCCAACTACC
TGAACTGGTACCAGCAGAAGCCCGGAAAGGCCCCGAAAGTGCTCATCTACTTCACCTCATCGCTGCACTCGGGAGTG
CCCTCAAGATTTTCCGGCTCCGGAAGCGGGACCGACTTCACTCTTACCATCTCATCGTTGCAACCAGAGGATTTCGC
GACCTACTACTGTCAGCAGTACTCCACGGTGCCGTGGACCTTCGGACAAGGCACCAAAGTGGAGATCAAGAGGACTG
TGGCGGCCCCGAGCGTGTTCATTTTCCCTCCTTCCGACGAGCAGCTGAAAAGCGGCACCGCCTCGGTCGTGTGCCTC
CTGAACAACTTCTACCCGCGGGAAGCCAAGGTCCAGTGGAAGGTCGACAACGCGCTGCAGAGCGGAAATTCCCAGGA
GAGCGTGACCGAACAGGACTCCAAGGACAGCACCTATTCCCTGTCGTCTACACTGACCCTGAGCAAGGCCGACTACG
AGAAGCATAAGGTCTACGCATGCGAAGTGACCCACCAAGGTCTTTCCTCCCCTGTGACCAAGTCCTTCAACCGGGGC
GAATGCTGA SEQ ID NO: 21, DNA sequence (LY2.55.1), for peptide L1-15 (no LE) fused to the
N-terminus of the light chain of Bevacizumab
ATGGCCTGGATGATGTTGCTTCTCGGACTTCTCGCGTATGGATCAGGGGTGGATAGCGCGCAACAGAAGTACCAGCC
TTTGGACGAACTGGACAAGACCCTGTACGACCAGTTCATGCTGCAACAGGGAGGGGCGGTGGATCCGGGGCGGCG
GCTCCGGCGGTGGCGGATCCGACATTCAAATGACTCAGTCGCCATCGTCCCTCTCGGCATCCGTGGGAGACAGAGTG
ACCATCACTTGTTCCGCCTCGCAAGACATCTCCAACTACCTGAACTGGTACCAGCAGAAGCCCGGGAAGGCCCCCAA
AGTGCTCATCTACTTTACTTCCTCACTGCACTCCGGGGTGCCAAGCCGCTTTAGCGGCTCCGGTTCTGGAACCGATT
TCACCCTGACCATTAGCTCACTCCAGCCGGAAGATTTCGCTACGTACTACTGCCAGCAGTATTCGACCGTGCCGTGG
ACTTTCGGACAGGGTACCAAAGTCGAGATCAAGCGGACCGTGGCCGCCCCGAGCGTGTTCATTTTCCCGCCTTCCGA
CGAGCAACTCAAGTCCGGCACTGCCTCCGTGGTCTGCCTGCTGAACAATTTCTACCCCGCGAGGCTAAGGTCCAGT
GGAAGGTCGATAACGCACTGCAGTCCGGAAACAGCCAAGAGCGTGACCGAACAGGACTCCAAGGACTCAACTTAC
TCGCTGAGCTCCACCCTGACCCTGTCGAAGGCCGACTACGAAAAGCACAAAGTGTACGCCTGCGAAGTGACACATCA
GGGCCTGTCATCCCCTGTCACCAAGTCCTTCAACCGGGGAGAGTGCTGATAA SEQ ID NO: 22, DNA sequence (LY2.55.2), for peptide L1-15 (with LE) fused to
the N-terminus of the light chain of Bevacizumab
ATGGCCTGGATGATGTTGCTTCTCGGACTTCTCGCGTATGGATCAGGGGTGGATAGCGCGCAACAGAAGTACCAGCC
TTTGGACGAACTGGACAAGACCCTGTACGACCAGTTCATGCTGCAACAGGGACTGGAAGGGGCGGTGGATCCGGGG
GCGGCGGCTCCGGCGGTGGCGGATCCGACATTCAAATGACTCAGTCGCCATCGTCCCTCTCGGCATCCGTGGGAGAC
AGAGTGACCATCACTTGTTCCGCCTCGCAAGACATCTCCAACTACCTGAACTGGTACCAGCAGAAGCCCGGGAAGGC
CCCCAAAGTGCTCATCTACTTTACTTCCTCACTGCACTCCGGGGTGCCAAGCCGCTTTAGCGGCTCCGGTTCTGGAA
CCGATTTCACCCTGACCATTAGCTCACTCCAGCCGGAAGATTTCGCTACGTACTACTGCCAGCAGTATTCGACCGTG
CCGTGGACTTTCGGACAGGGTACCAAAGTCGAGATCAAGCGGACCGTGGCCGCCCCGAGCGTGTTCATTTTCCCGCC
TTCCGACGAGCAACTCAAGTCCGGCACTGCCTCCGTGGTCTGCCTGCTGAACAATTTCTACCCCGCGAGGCTAAGG
TCCAGTGGAAGGTCGATAACGCACTGCAGTCCGGAAACAGCCAAGAGAGCGTGACCGAACAGGACTCCAAGGACTCA
ACTTACTCGCTGAGCTCCACCCTGACCCTGTCGAAGGCCGACTACGAAAAGCACAAAGTGTACGCCTGCGAAGTGAC
ACATCAGGGCCTGTCATCCCCTGTCACCAAGTCCTTCAACCGGGGAGAGTGCTGATAA

| SEQUENCES |
| --- |

SEQ ID NO: 23, DNA sequence (LY2.55.3), for peptide L1-15 (no LE) fused to the
N-terminus of the heavy chain of Bevacizumab
ATGGCTTGGATGATGCTGCTGCTTGGCCTTCTCGCATACGGTTCCGGAGTCGATAGCGCCCAACAGAAGTACCAGCC
TCTGGACGAACTGGATAAGACCCTGTACGATCAGTTCATGCTGCAACAGGGGGGCGGCGGAGGATCGGGCGGTGGTG
GATCCGGCGGCGGCGGATCCGAAGTGCAGCTCGTGGAGAGCGGGGGCGGACTCGTGCAGCCGGGAGGTTCGCTGAGA
TTGTCCTGTGCCGCCTCCGGTTACACCTTTACCAATTACGGGATGAACTGGGTCCGCCAGGCCCCCGGAAAGGGACT
GGAATGGGTCGGCTGGATCAACACATATACCGGAGAGCCCACCTACGCCGCGGACTTCAAGCGGAGATTCACCTTTT
CACTGGATACGTCAAAGTCAACTGCATACCTCCAGATGAACTCCCTTAGGGCGGAAGATACCGCCGTGTACTACTGC
GCCAAGTACCCGCACTATTACGGGTCCAGCCATTGGTACTTCGACGTCTGGGGACAGGGGACCCTCGTGACCGTCAG
CAGCGCCTCCACCAAGGGCCCGTCCGTGTTCCCTCTTGCGCCGTCGTCCAAAAGCACTTCCGGCGGCACTGCCGCCC
TGGGCTGCCTCGTGAAGGATTACTTCCCGGAACCGGTCACCGTGTCGTGGAACTCCGGAGCCCTGACTTCGGGTGTC
CACACCTTCCCTGCGGTGCTGCAGAGCTCCGGTCTGTACTCCCTCTCTTCCGTGGTCACGGTGCCCTCCTCATCACT
GGGAACCCAGACCTACATCTGCAACGTGAACCACAAGCCCTCAAACACTAAGGTCGACAAGAAAGTCGAACCGAAGT
CGTGCGACAAGACCCACACTTGCCCTCCGTGCCCGGCTCCCGAGCTGCTGGGGGGCCCTTCCGTGTTTTTGTTCCCG
CCGAAACCAAAGGACACTCTGATGATCAGCCGCACTCCGGAAGTGACCTGTGTGGTGGTGGACGTGTCCCACGAGGA
CCCAGAAGTGAAATTCAATTGGTACGTGGATGGCGTGGAAGTGCACAACGCTAAGACTAAGCCCCGCGAGGAACAGT
ACAACAGCACTTACCGGGTGGTGTCGGTGCTCACCGTGCTGCACCAAGATTGGCTCAACGGGAAGGAGTACAAGTGC
AAAGTCTCCAACAAGGCCCTGCCCGCACCTATTGAAAAGACCATCAGCAAGGCCAAGGGACAGCCCCGGGAGCCCCA
GGTCTACACCCTGCCTCCCTCGCGCGAAGAGATGACTAAGAACCAAGTGTCCCTGACCTGTCTGGTCAAGGGATTCT
ATCCTTCCGACATTGCCGTGGAATGGGAGTCCAACGGGCAGCCAGAGAACAACTACAAGACCACTCCACCTGTGCTG
GACTCCGACGGGTCCTTCTTCTTGTACTCGAAGCTGACCGTGGACAAGTCCCGGTGGCAGCAGGGAAACGTGTTCAG
CTGCTCCGTGATGCACGAGGCCTTGCATAATCATTACACCCAAAAGTCGCTGAGCTTGAGCCCGGGAAAGTGATAA SEQ ID NO: 24, DNA sequence (LY2.55.4), for peptide L1-15 (with LE) fused to
the N-terminus of the heavy chain of Bevacizumab
ATGGCTTGGATGATGCTGCTGCTTGGCCTTCTCGCATACGGTTCCGGAGTCGATAGCGCCCAACAGAAGTACCAGCC
TCTGGACGAACTGGATAAGACCCTGTACGATCAGTTCATGCTGCAACAGGGGGGCTTGAGGCGTTGGCGGAGGATCGGGCG
GTGGTGGATCCGGCGGCGGCGGATCCGAAGTGCAGCTCGTGGAGAGCGGGGGCGGACTCGTGCAGCCGGGAGGTTCG
CTGAGATTGTCCTGTGCCGCCTCCGGTTACACCTTTACCAATTACGGGATGAACTGGGTCCGCCAGGCCCCCGGAAA
GGGACTGGAATGGGTCGGCTGGATCAACACATATACCGGAGAGCCCACCTACGCCGCGGACTTCAAGCGGAGATTCA
CCTTTTCACTGGATACGTCAAAGTCAACTGCATACCTCCAGATGAACTCCCTTAGGGCGGAAGATACCGCCGTGTAC
TACTGCGCCAAGTACCCGCACTATTACGGGTCCAGCCATTGGTACTTCGACGTCTGGGGACAGGGGACCCTCGTGAC
CGTCAGCAGCGCCTCCACCAAGGGCCCGTCCGTGTTCCCTCTTGCGCCGTCGTCCAAAAGCACTTCCGGCGGCACTG
CCGCCCTGGGCTGCCTCGTGAAGGATTACTTCCCGGAACCGGTCACCGTGTCGTGGAACTCCGGAGCCCTGACTTCG
GGTGTCCACACCTTCCCTGCGGTGCTGCAGAGCTCCGGTCTGTACTCCCTCTCTTCCGTGGTCACGGTGCCCTCCTC
ATCACTGGGAACCCAGACCTACATCTGCAACGTGAACCACAAGCCCTCAAACACTAAGGTCGACAAGAAAGTCGAAC
CGAAGTCGTGCGACAAGACCCACACTTGCCCTCCGTGCCCGGCTCCCGAGCTGCTGGGGGGCCCTTCCGTGTTTTTG
TTCCCGCCGAAACCAAAGGACACTCTGATGATCAGCCGCACTCCGGAAGTGACCTGTGTGGTGGTGGACGTGTCCCA
CGAGGACCCAGAAGTGAAATTCAATTGGTACGTGGATGGCGTGGAAGTGCACAACGCTAAGACTAAGCCCCGCGAGG
AACAGTACAACAGCACTTACCGGGTGGTGTCGGTGCTCACCGTGCTGCACCAAGATTGGCTCAACGGGAAGGAGTAC
AAGTGCAAAGTCTCCAACAAGGCCCTGCCCGCACCTATTGAAAAGACCATCAGCAAGGCCAAGGGACAGCCCCGGGA
GCCCCAGGTCTACACCCTGCCTCCCTCGCGCGAAGAGATGACTAAGAACCAAGTGTCCCTGACCTGTCTGGTCAAGG
GATTCTATCCTTCCGACATTGCCGTGGAATGGGAGTCCAACGGGCAGCCAGAGAACAACTACAAGACCACTCCACCT
GTGCTGGACTCCGACGGGTCCTTCTTCTTGTACTCGAAGCTGACCGTGGACAAGTCCCGGTGGCAGCAGGGAAACGT
GTTCAGCTGCTCCGTGATGCACGAGGCCTTGCATAATCATTACACCCAAAAGTCGCTGAGCTTGAGCCCGGGAAAGT
GATAA SEQ ID NO: 25, DNA sequence (LY2.55.5), for the light chain of Bevacizumab
ATGGCCTGGATGATGTTGCTTCTCGGACTTCTCGCGTATGGATCAGGGGTGGACTCCGACATTCAAATGACTCAGTC
GCCATCGTCCCTCTCGGCATCGTGGGAGACAGAGTGACCATCACTTGTTCCGCCTCGCAAGACATCTCCAACTACC
TGAACTGGTACCAGCAGAAGCCCGGGAAGGCCCCCAAAGTGCTCATCTACTTTACTTCCTCACTGCACTCCGGGGTG
CCAAGCCGCTTTAGCGGCTCCGGTTCTGGAACCGATTTCACCCTGACCATTAGCTCACTCCAGCCGGAAGATTTCGC
TACGTACTACTGCCAGCAGTATTCGACCGTGCCGTGGACTTTCGGACAGGGTACCAAAGTCGAGATCAAGCGGACCG
TGGCCGCCCCGAGCGTGTTCATTTTCCCGCCTTCCGACGAGCAACTCAAGTCCGGCACTGCCTCCGTGGTCTGCCTG
CTGAACAATTTCTACCCCCGCGAGGCTAAGGTCCAGTGGAAGGTCGATAACGCACTGCAGTCCGGAAACAGCCAAGA
GAGCGTGACCGAACAGGACTCCAAGGACTCAACTTACTCGCTGAGCTCCACCCTGACCCTGTCGAAGGCCGACTACG
AAAAGCACAAAGTGTACGCCTGCGAAGTGACACATCAGGGCCTGTCATCCCTGTCACCAAGTCCTTCAACCGGGGA
GAGTGCTGATAA

| SEQUENCE LISTING |
| --- |

<160> NUMBER OF SEQ ID NOS: 25

<210> SEQ ID NO 1
<211> LENGTH: 59
<212> TYPE: PRT
<213> ORGANISM: Artificial Sequence
<220> FEATURE:
<223> OTHER INFORMATION: Peptide Fragment of Angiopoietin-2

<400> SEQUENCE: 1

Gly Gly Gly Gly Gly Ala Gln Gln Glu Glu Cys Glu Trp Asp Pro Trp
1               5                   10                  15

Thr Cys Glu His Met Gly Ser Ser Ala Thr Gly Ser Gly Ser
        20              25                  30

Thr Ala Ser Ser Gly Ser Gly Ser Ala Thr His Gln Glu Glu Cys Glu
        35              40                  45

Trp Asp Pro Trp Thr Cys Glu His Met Leu Glu
50                  55

<210> SEQ ID NO 2
<211> LENGTH: 453
<212> TYPE: PRT
<213> ORGANISM: Artificial Sequence
<220> FEATURE:
<223> OTHER INFORMATION: Heavy Chain of Bevacizumab

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 3
<211> LENGTH: 214
<212> TYPE: PRT
<213> ORGANISM: Artificial Sequence
<220> FEATURE:
<223> OTHER INFORMATION: Light Chain of Bevacizumab

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205
```

Phe Asn Arg Gly Glu Cys
    210

<210> SEQ ID NO 4
<211> LENGTH: 512
<212> TYPE: PRT
<213> ORGANISM: Artificial Sequence
<220> FEATURE:
<223> OTHER INFORMATION: Fusion protein of 2xCon4(C) fused to the
      C-terminus of the Bevacizumab heavy chain

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

-continued

```
Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Gly Ala Gln Gln Glu Glu Cys
            450                 455                 460

Glu Trp Asp Pro Trp Thr Cys Glu His Met Gly Ser Gly Ser Ala Thr
465                 470                 475                 480

Gly Gly Ser Gly Ser Thr Ala Ser Ser Gly Ser Gly Ser Ala Thr His
                485                 490                 495

Gln Glu Glu Cys Glu Trp Asp Pro Trp Thr Cys Glu His Met Leu Glu
            500                 505                 510
```

<210> SEQ ID NO 5
<211> LENGTH: 431
<212> TYPE: PRT
<213> ORGANISM: Artificial Sequence
<220> FEATURE:
<223> OTHER INFORMATION: VEGF Trap Aflibercept
<220> FEATURE:
<221> NAME/KEY: VARIANT
<222> LOCATION: (431)..(431)
<223> OTHER INFORMATION: X is G or K

<400> SEQUENCE: 5

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
```

```
            180                 185                 190
Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Xaa
            420                 425                 430

<210> SEQ ID NO 6
<211> LENGTH: 491
<212> TYPE: PRT
<213> ORGANISM: Artificial Sequence
<220> FEATURE:
<223> OTHER INFORMATION: Fusion protein of 2xCon4(C) fused to the
      C-terminus of the VEGF Trap

<400> SEQUENCE: 6

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110
```

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
        130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
275                 280                 285

Ser Val Leu Thr Val Leu His Gln Asp Trp Leu Asn Gly Lys Glu Tyr
        290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

Gly Gly Gly Gly Gly Ala Gln Gln Glu Glu Cys Glu Trp Asp Pro Trp
        435                 440                 445

Thr Cys Glu His Met Gly Ser Gly Ser Ala Thr Gly Gly Ser Gly Ser
450                 455                 460

Thr Ala Ser Ser Gly Ser Gly Ser Ala Thr His Gln Glu Glu Cys Glu
465                 470                 475                 480

Trp Asp Pro Trp Thr Cys Glu His Met Leu Glu
                485                 490

<210> SEQ ID NO 7
<211> LENGTH: 25
<212> TYPE: PRT
<213> ORGANISM: Artificial Sequence
<220> FEATURE:
<223> OTHER INFORMATION: L1-7 Angiopoietin-2 binding peptide

<400> SEQUENCE: 7

Ala Gln Gln Thr Asn Phe Met Pro Met Asp Asp Leu Glu Gln Arg Leu
1               5                   10                  15

Tyr Glu Gln Phe Ile Leu Gln Gln Gly
            20                  25

<210> SEQ ID NO 8
<211> LENGTH: 24
<212> TYPE: PRT
<213> ORGANISM: Artificial Sequence
<220> FEATURE:
<223> OTHER INFORMATION: L1-10 Angiopoietin-2 binding peptide

<400> SEQUENCE: 8

Ala Gln Gln Lys Phe Gln Pro Leu Asp Glu Leu Glu Gln Thr Leu Tyr
1               5                   10                  15

Glu Gln Phe Met Leu Gln Gln Ala
            20

<210> SEQ ID NO 9
<211> LENGTH: 24
<212> TYPE: PRT
<213> ORGANISM: Artificial Sequence
<220> FEATURE:
<223> OTHER INFORMATION: L1-15 Angiopoietin-2 binding peptide

<400> SEQUENCE: 9

Ala Gln Gln Lys Tyr Gln Pro Leu Asp Glu Leu Asp Lys Thr Leu Tyr
1               5                   10                  15

Asp Gln Phe Met Leu Gln Gln Gly
            20

<210> SEQ ID NO 10
<211> LENGTH: 23
<212> TYPE: PRT
<213> ORGANISM: Artificial Sequence
<220> FEATURE:
<223> OTHER INFORMATION: L1-7B Angiopoietin-2 binding peptide

<400> SEQUENCE: 10

Gln Thr Asn Phe Met Pro Met Asp Asp Leu Glu Gln Arg Leu Tyr Glu
1               5                   10                  15

Gln Phe Ile Leu Gln Gln Gly
            20

<210> SEQ ID NO 11
<211> LENGTH: 22
<212> TYPE: PRT
<213> ORGANISM: Artificial Sequence
<220> FEATURE:
<223> OTHER INFORMATION: L1-10B Angiopoietin-2 binding peptide

<400> SEQUENCE: 11

Gln Lys Phe Gln Pro Leu Asp Glu Leu Glu Gln Thr Leu Tyr Glu Gln
1               5                   10                  15

Phe Met Leu Gln Gln Ala
            20

<210> SEQ ID NO 12
<211> LENGTH: 22
<212> TYPE: PRT
<213> ORGANISM: Artificial Sequence
<220> FEATURE:

<223> OTHER INFORMATION: L1-15B Angiopoietin-2 binding peptide

<400> SEQUENCE: 12

Gln Lys Tyr Gln Pro Leu Asp Glu Leu Asp Lys Thr Leu Tyr Asp Gln
1               5                   10                  15

Phe Met Leu Gln Gln Gly
            20

<210> SEQ ID NO 13
<211> LENGTH: 5
<212> TYPE: PRT
<213> ORGANISM: Artificial Sequence
<220> FEATURE:
<223> OTHER INFORMATION: Linker Angiopoietin-2 binding peptide

<400> SEQUENCE: 13

Gly Gly Gly Gly Ser
1               5

<210> SEQ ID NO 14
<211> LENGTH: 253
<212> TYPE: PRT
<213> ORGANISM: Artificial Sequence
<220> FEATURE:
<223> OTHER INFORMATION: L1-15/Light Chain Fusion molecule

<400> SEQUENCE: 14

Ala Gln Gln Lys Tyr Gln Pro Leu Asp Glu Leu Asp Lys Thr Leu Tyr
1               5                   10                  15

Asp Gln Phe Met Leu Gln Gln Gly Gly Gly Gly Ser Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Ser Ala
    50                  55                  60

Ser Gln Asp Ile Ser Asn Tyr Leu Asn Trp Tyr Gln Gln Lys Pro Gly
65                  70                  75                  80

Lys Ala Pro Lys Val Leu Ile Tyr Phe Thr Ser Ser Leu His Ser Gly
                85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Phe Ala Thr Tyr Tyr Cys Gln
        115                 120                 125

Gln Tyr Ser Thr Val Pro Trp Thr Phe Gly Gln Gly Thr Lys Val Glu
    130                 135                 140

Ile Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250

-continued

```
                245                 250

<210> SEQ ID NO 15
<211> LENGTH: 492
<212> TYPE: PRT
<213> ORGANISM: Artificial Sequence
<220> FEATURE:
<223> OTHER INFORMATION: L1-15 Heavy Chain Fusion Molecule

<400> SEQUENCE: 15

Ala Gln Gln Lys Tyr Gln Pro Leu Asp Glu Leu Asp Lys Thr Leu Tyr
1               5                   10                  15

Asp Gln Phe Met Leu Gln Gln Gly Gly Gly Gly Ser Gly Gly Gly
            20                  25                  30

Gly Ser Gly Gly Gly Ser Glu Val Gln Leu Val Glu Ser Gly Gly
        35                  40                  45

Gly Leu Val Gln Pro Gly Gly Ser Leu Arg Leu Ser Cys Ala Ala Ser
    50                  55                  60

Gly Tyr Thr Phe Thr Asn Tyr Gly Met Asn Trp Val Arg Gln Ala Pro
65                  70                  75                  80

Gly Lys Gly Leu Glu Trp Val Gly Trp Ile Asn Thr Tyr Thr Gly Glu
                85                  90                  95

Pro Thr Tyr Ala Ala Asp Phe Lys Arg Arg Phe Thr Phe Ser Leu Asp
            100                 105                 110

Thr Ser Lys Ser Thr Ala Tyr Leu Gln Met Asn Ser Leu Arg Ala Glu
        115                 120                 125

Asp Thr Ala Val Tyr Tyr Cys Ala Lys Tyr Pro His Tyr Tyr Gly Ser
    130                 135                 140

Ser His Trp Tyr Phe Asp Val Trp Gly Gln Gly Thr Leu Val Thr Val
145                 150                 155                 160

Ser Ser Ala Ser Thr Lys Gly Pro Ser Val Phe Pro Leu Ala Pro Ser
                165                 170                 175

Ser Lys Ser Thr Ser Gly Gly Thr Ala Ala Leu Gly Cys Leu Val Lys
            180                 185                 190

Asp Tyr Phe Pro Glu Pro Val Thr Val Ser Trp Asn Ser Gly Ala Leu
        195                 200                 205

Thr Ser Gly Val His Thr Phe Pro Ala Val Leu Gln Ser Ser Gly Leu
    210                 215                 220

Tyr Ser Leu Ser Ser Val Val Thr Val Pro Ser Ser Ser Leu Gly Thr
225                 230                 235                 240

Gln Thr Tyr Ile Cys Asn Val Asn His Lys Pro Ser Asn Thr Lys Val
                245                 250                 255

Asp Lys Lys Val Glu Pro Lys Ser Cys Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
```

```
                  355                 360                 365
Ser Asn Lys Ala Leu Pro Ala Pro Ile Glu Lys Thr Ile Ser Lys Ala
370                 375                 380

Lys Gly Gln Pro Arg Glu Pro Gln Val Tyr Thr Leu Pro Pro Ser Arg
385                 390                 395                 400

Glu Glu Met Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 16
<211> LENGTH: 494
<212> TYPE: PRT
<213> ORGANISM: Artificial Sequence
<220> FEATURE:
<223> OTHER INFORMATION: L1-15 with LE Heavy Chain Fusion Molecule

<400> SEQUENCE: 16

Ala Gln Gln Lys Tyr Gln Pro Leu Asp Glu Leu Asp Lys Thr Leu Tyr
1               5                   10                  15

Asp Gln Phe Met Leu Gln Gln Leu Glu Gly Gly Gly Gly Ser Gly
            20                  25                  30

Gly Gly Gly Ser Gly Gly Gly Ser Glu Val Gln Leu Val Glu Ser
        35                  40                  45

Gly Gly Gly Leu Val Gln Pro Gly Gly Ser Leu Arg Leu Ser Cys Ala
    50                  55                  60

Ala Ser Gly Tyr Thr Phe Thr Asn Tyr Gly Met Asn Trp Val Arg Gln
65                  70                  75                  80

Ala Pro Gly Lys Gly Leu Glu Trp Val Gly Trp Ile Asn Thr Tyr Thr
                85                  90                  95

Gly Glu Pro Thr Tyr Ala Ala Asp Phe Lys Arg Arg Phe Thr Phe Ser
            100                 105                 110

Leu Asp Thr Ser Lys Ser Thr Ala Tyr Leu Gln Met Asn Ser Leu Arg
        115                 120                 125

Ala Glu Asp Thr Ala Val Tyr Tyr Cys Ala Lys Tyr Pro His Tyr Tyr
    130                 135                 140

Gly Ser Ser His Trp Tyr Phe Asp Val Trp Gly Gln Gly Thr Leu Val
145                 150                 155                 160

Thr Val Ser Ser Ala Ser Thr Lys Gly Pro Ser Val Phe Pro Leu Ala
                165                 170                 175

Pro Ser Ser Lys Ser Thr Ser Gly Gly Thr Ala Ala Leu Gly Cys Leu
            180                 185                 190

Val Lys Asp Tyr Phe Pro Glu Pro Val Thr Val Ser Trp Asn Ser Gly
        195                 200                 205

Ala Leu Thr Ser Gly Val His Thr Phe Pro Ala Val Leu Gln Ser Ser
    210                 215                 220

Gly Leu Tyr Ser Leu Ser Ser Val Val Thr Val Pro Ser Ser Ser Leu
```

-continued

```
                225                 230                 235                 240
Gly Thr Gln Thr Tyr Ile Cys Asn Val Asn His Lys Pro Ser Asn Thr
            245                 250                 255

Lys Val Asp Lys Lys Val Glu Pro Lys Ser Cys Asp Lys Thr His Thr
                260                 265                 270

Cys Pro Pro Cys Pro Ala Pro Glu Leu Leu Gly Gly Pro Ser Val Phe
            275                 280                 285

Leu Phe Pro Pro Lys Pro Lys Asp Thr Leu Met Ile Ser Arg Thr Pro
290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Arg Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys
                485                 490

<210> SEQ ID NO 17
<211> LENGTH: 508
<212> TYPE: PRT
<213> ORGANISM: Artificial Sequence
<220> FEATURE:
<223> OTHER INFORMATION: Fusion protein of 2xCon4(C) fused to the
      C-terminus of the Heavy Chain of Bevacizumab, with linker peptide
      GGGGSGGGGSGGGGS

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95
```

```
Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys Gly Gly Gly Gly Ala Gln Gln Glu Glu Cys
            450                 455                 460

Glu Trp Asp Pro Trp Thr Cys Glu His Met Gly Gly Gly Ser Gly
465                 470                 475                 480

Gly Gly Gly Ser Gly Gly Gly Ser Ala Thr His Gln Glu Glu Cys
                485                 490                 495

Glu Trp Asp Pro Trp Thr Cys Glu His Met Leu Glu
            500                 505
```

<210> SEQ ID NO 18
<211> LENGTH: 471
<212> TYPE: PRT
<213> ORGANISM: Artificial Sequence
<220> FEATURE:
<223> OTHER INFORMATION: L1-15 fused to the N-terminus of the VEGF Trap, with linker peptide GGGGSGGGGSGGGGS

<400> SEQUENCE: 18

```
Ala Gln Gln Lys Tyr Gln Pro Leu Asp Glu Leu Asp Lys Thr Leu Tyr
1               5                   10                  15

Asp Gln Phe Met Leu Gln Gln Gly Gly Gly Gly Ser Gly Gly Gly Gly
            20                  25                  30

Gly Ser Gly Gly Gly Gly Ser Ser Asp Thr Gly Arg Pro Phe Val Glu
        35                  40                  45

Met Tyr Ser Glu Ile Pro Glu Ile Ile His Met Thr Glu Gly Arg Glu
    50                  55                  60

Leu Val Ile Pro Cys Arg Val Thr Ser Pro Asn Ile Thr Val Thr Leu
65                  70                  75                  80

Lys Lys Phe Pro Leu Asp Thr Leu Ile Pro Asp Gly Lys Arg Ile Ile
                85                  90                  95

Trp Asp Ser Arg Lys Gly Phe Ile Ile Ser Asn Ala Thr Tyr Lys Glu
            100                 105                 110

Ile Gly Leu Leu Thr Cys Glu Ala Thr Val Asn Gly His Leu Tyr Lys
        115                 120                 125

Thr Asn Tyr Leu Thr His Arg Gln Thr Asn Thr Ile Ile Asp Val Val
    130                 135                 140

Leu Ser Pro Ser His Gly Ile Glu Leu Ser Val Gly Glu Lys Leu Val
145                 150                 155                 160

Leu Asn Cys Thr Ala Arg Thr Glu Leu Asn Val Gly Ile Asp Phe Asn
                165                 170                 175

Trp Glu Tyr Pro Ser Ser Lys His Gln His Lys Lys Leu Val Asn Arg
            180                 185                 190

Asp Leu Lys Thr Gln Ser Gly Ser Glu Met Lys Lys Phe Leu Ser Thr
        195                 200                 205

Leu Thr Ile Asp Gly Val Thr Arg Ser Asp Gln Gly Leu Tyr Thr Cys
    210                 215                 220

Ala Ala Ser Ser Gly Leu Met Thr Lys Lys Asn Ser Thr Phe Val Arg
225                 230                 235                 240

Val His Glu Lys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365
```

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 19
<211> LENGTH: 1584
<212> TYPE: DNA
<213> ORGANISM: Artificial Sequence
<220> FEATURE:
<223> OTHER INFORMATION: DNA sequence (DHAMDH02083016) for 2xCon4(C)
      fused to the C-terminus of the Heavy Chain of Bevacizumab, with
      linker peptide GGGGSGGGGSGGGGS

<400> SEQUENCE: 19
atgggttggt cctgtatcat tcttttcctc gtcgccactg ccaccggagt ccactcagaa      60
gtccagttgg tggagtcggg aggaggactg gtgcagccag cggctccct gcgcctgtcc     120 tgcgcggcgt ccgggtacac cttcaccaac tacggcatga ctgggtccg ccaggccccc     180 ggaaaggggc tggaatgggt cggctggatc aacacttaca ccggagaacc tacctacgct     240
gccgatttca gcggcgctt tactttctcg ctggacacct ccaagagcac cgcctatctc     300
caaatgaact ccctgcgggc cgaggatacc gccgtgtact attgcgcgaa gtaccccac     360 tattacggtt cgtcccattg gtacttcgac gtctggggcc agggaactct tgtcactgtg     420
tcctccgcat ccaccaaggg accgtcagtg ttccccctgg ccccgtcctc caaaagcact     480
agcggaggaa ccgcagcctt gggatgcctc gtcaaggact actttcccga gcctgtcacc     540
gtgtcgtgga actccggtgc cctcacttcg ggcgtgcaca cgttcccagc ggtgctgcag     600
tccagcggac tgtactcgct gtcctccgtc gtgaccgtgc cttcatcgag cctggggacc     660
cagacctaca tttgcaacgt gaaccacaag ccctccaaca ccaaagtgga caagaaggtc     720
gaaccaaaga gctgcgacaa gacccacact tgcccgccgt gccggcccc tgagttgctg     780 ggtggtccat cggtgttcct gttcccgcct aagccgaagg acacactcat gatcagcagg     840 accccgaag tgacctgtgt ggtggtcgac gtgtcacatg aagatcccga ggtcaagttc     900
aattggtacg tggacggagt ggaagtgcat aatgccaaga ctaagccgag agaggaacag     960
tacaactcca cctaccgggt ggtgtcagtg ctgaccgtgc tccatcagga ctggctcaac    1020
gggaaggagt acaagtgcaa agtgtcgaac aaggctctcc ccgcccctat cgagaaaacc    1080
attagcaagg ctaagggaca gccgcgggag ccgcaagtgt acaccctgcc ccgagccgc    1140 gaagaaatga ctaagaacca agtgtccctg acctgtctcg tgaaagggtt ctacccgtcg    1200
gacatcgctg tggagtggga gtctaatggt caacctgaga caactacaa gactactccc    1260 cctgtgctgg actccgatgg ttccttttc ctgtactcaa agctgaccgt ggacaagtcc    1320
agatggcagc agggcaacgt gttcagctgc tccgtgatgc atgaagcact tcacaaccac    1380

```
tacacccaga agtccctcag cctgtctccg gggaagggcg gcggaggagg ggcccagcag    1440
gaagagtgtg aatgggaccc ctggacttgt gaacacatgg gcggcggcgg ctccggtgga    1500
ggaggatccg gcggaggggg cagcgcgacg caccaggagg agtgcgaatg ggatccatgg    1560
acttgcgaac acatgctgga gtga                                           1584

<210> SEQ ID NO 20
<211> LENGTH: 702
<212> TYPE: DNA
<213> ORGANISM: Artificial Sequence
<220> FEATURE:
<223> OTHER INFORMATION: DNA sequence (DHAMDL083016), for the light
      chain of Bevacizumab

<400> SEQUENCE: 20
atgggttggt cctgtattat cctctttctc gtcgccactg ccaccggagt gcactcagat      60
attcagatga cccagagccc ctcctcactg tccgcttccg tggggggaccg cgtgactatc    120 acttgctcgg cttcccaaga tatctccaac tacctgaact ggtaccagca gaagcccgga    180
aaggccccga agtgctcat ctacttcacc tcatcgctgc actcgggagt gccctcaaga     240 tttttccggct ccggaagcgg gaccgacttc actcttacca tctcatcgtt gcaaccagag    300
gatttcgcga cctactactg tcagcagtac tccacggtgc cgtggacctt cggacaaggc    360
accaaagtgg agatcaagag gactgtggcg gcccccgagc tgttcatttt ccctccttcc    420
gacgagcagc tgaaaagcgg caccgcctcg gtcgtgtgcc tcctgaacaa cttctacccg    480
cgggaagcca aggtccagtg gaaggtcgac aacgcgctgc agagcggaaa ttcccaggag    540
agcgtgaccg aacaggactc caaggacagc acctattccc tgtcgtctac actgaccctg    600
agcaaggccg actacgagaa gcataaggtc tacgcatgcg aagtgaccca ccaaggtctt    660
tcctcccctg tgaccaagtc cttcaaccgg ggcgaatgct ga                        702

<210> SEQ ID NO 21
<211> LENGTH: 822
<212> TYPE: DNA
<213> ORGANISM: Artificial Sequence
<220> FEATURE:
<223> OTHER INFORMATION: , DNA sequence (LY2.55.1), for peptide L1-15
      (no LE) fused to the N-terminus of the light chain of Bevacizumab

<400> SEQUENCE: 21
atggcctgga tgatgttgct tctcggactt ctcgcgtatg atcagggggt ggatagcgcg      60
caacagaagt accagccttt ggacgaactg gacaagaccc tgtacgacca gttcatgctg    120
caacagggag ggggcggtgg atccgggggc ggcggctccg gcggtggcgg atccgacatt    180
caaatgactc agtcgccatc gtccctctcg gcatccgtgg gagacagagt gaccatcact    240
tgttccgcct cgcaagacat ctccaactac ctgaactggt accagcagaa gcccgggaag    300
gcccccaaag tgctcatcta cttactttcc tcactgcact ccggggtgcc aagccgcttt    360
agcggctccg gttctggaac cgatttcacc ctgaccatta gctcactcca gccggaagat    420
ttcgctacgt actactgcca gcagtattcg accgtgccgt ggactttcgg acagggtacc    480
aaagtcgaga tcaagcggac cgtggccgcc ccgagcgtgt tcatttttccc gccttccgac    540 gagcaactca gtccggcac tgcctccgtg gtctgcctgc tgaacaattt ctaccccgc      600 gaggctaagg tccagtggaa ggtcgataac gcactgcagt ccggaaacag ccaagagagc    660
gtgaccgaac aggactccaa ggactcaact tactcgctga gctccaccct gaccctgtcg    720
```
aaggccgact acgaaaagca caaagtgtac gcctgcgaag tgacacatca gggcctgtca    780
tcccctgtca ccaagtcctt caaccgggga gagtgctgat aa    822

<210> SEQ ID NO 22
<211> LENGTH: 828
<212> TYPE: DNA
<213> ORGANISM: Artificial Sequence
<220> FEATURE:
<223> OTHER INFORMATION: DNA sequence (LY2.55.2), for peptide L1-15
      (with LE) fused to the N-terminus of the light chain of
      Bevacizumab

<400> SEQUENCE: 22
atggcctgga tgatgttgct tctcggactt ctcgcgtatg gatcaggggt ggatagcgcg    60
caacagaagt accagccttt ggacgaactg gacaagaccc tgtacgacca gttcatgctg    120
caacagggac tggaaggggg cggtggatcc ggggcggcg gctccggcgg tggcggatcc    180
gacattcaaa tgactcagtc gccatcgtcc ctctcggcat ccgtgggaga cagagtgacc    240
atcacttgtt ccgcctcgca agacatctcc aactacctga actggtacca gcagaagccc    300
gggaaggccc ccaaagtgct catctacttt acttcctcac tgcactccgg ggtgccaagc    360
cgctttagcg gctccggttc tggaaccgat ttcaccctga ccattagctc actccagccg    420
gaagatttcg ctacgtacta ctgccagcag tattcgaccg tgccgtggac tttcggacag    480
ggtaccaaag tcgagatcaa gcggaccgtg gccgccccga gcgtgttcat tttcccgcct    540
tccgacgagc aactcaagtc cggcactgcc tccgtggtct gcctgctgaa caatttctac    600
ccccgcgagg ctaaggtcca gtggaaggtc gataacgcac tgcagtccgg aaacagccaa    660
gagagcgtga ccgaacagga ctccaaggac tcaacttact cgctgagctc accctgacc    720 ctgtcgaagg ccgactacga aaagcacaaa gtgtacgcct gcgaagtgac acatcagggc    780
ctgtcatccc ctgtcaccaa gtccttcaac cggggagagt gctgataa    828

<210> SEQ ID NO 23
<211> LENGTH: 1539
<212> TYPE: DNA
<213> ORGANISM: Artificial Sequence
<220> FEATURE:
<223> OTHER INFORMATION: DNA sequence (LY2.55.3), for peptide L1-15 (no
      LE) fused to the N-terminus of the heavy chain of Bevacizumab

<400> SEQUENCE: 23
atggcttgga tgatgctgct gcttggcctt ctcgcatacg gttccggagt cgatagcgcc    60
caacagaagt accagcctct ggacgaactg gataagaccc tgtacgatca gttcatgctg    120 caacagggg gcggcggagg atcgggcggt ggtggatccg gcggcggcgg atccgaagtg    180
cagctcgtgg agagcggggg cggactcgtg cagccgggag gttcgctgag attgtcctgt    240
gccgcctccg gttacacctt taccaattac gggatgaact gggtccgcca ggcccccgga    300
aagggactgg aatgggtcgg ctggatcaac acatataccg agagcccac ctacgccgcg    360 gacttcaagc ggagattcac cttttcactg gatacgtcaa agtcaactgc ataccttcag    420
atgaactccc ttagggcgga agataccgcc gtgtactact gcgccaagta cccgcactat    480
tacgggtcca gccattggta cttcgacgtc tggggacagg gaccctcgt gaccgtcagc    540 agcgcctcca ccaagggccc gtccgtgttc cctcttgcgc cgtcgtccaa aagcacttcc    600
ggcggcactg ccgccctggg ctgcctcgtg aaggattact tcccggaacc ggtcaccgtg    660
tcgtggaact ccggagccct gacttcgggt gtccacacct ccctgcggt gctgcagagc    720

```
tccggtctgt actccctctc ttccgtggtc acggtgccct cctcatcact gggaacccag    780
acctacatct gcaacgtgaa ccacaagccc tcaaacacta aggtcgacaa gaaagtcgaa    840
ccgaagtcgt gcgacaagac ccacacttgc cctccgtgcc cggctcccga gctgctgggg    900
ggcccttccg tgttttttgtt cccgccgaaa ccaaaggaca ctctgatgat cagccgcact    960
ccggaagtga cctgtgtggt ggtggacgtg tcccacgagg acccagaagt gaaattcaat   1020
tggtacgtgg atggcgtgga agtgcacaac gctaagacta agccccgcga ggaacagtac   1080
aacagcactt accgggtggt gtcggtgctc accgtgctgc accaagattg gctcaacggg   1140
aaggagtaca agtgcaaagt ctccaacaag gccctgcccg cacctattga aaagaccatc   1200
agcaaggcca agggacagcc ccgggagccc caggtctaca ccctgcctcc ctcgcgcgaa   1260
gagatgacta agaaccaagt gtccctgacc tgtctggtca agggattcta tccttccgac   1320
attgccgtgg aatgggagtc aacgggcag ccagagaaca actacaagac cactccacct   1380
gtgctggact ccgacgggtc cttcttcttg tactcgaagc tgaccgtgga caagtcccgg   1440
tggcagcagg gaaacgtgtt cagctgctcc gtgatgcacg aggccttgca taatcattac   1500
acccaaaagt cgctgagctt gagcccggga aagtgataa                          1539
```

<210> SEQ ID NO 24
<211> LENGTH: 1545
<212> TYPE: DNA
<213> ORGANISM: Artificial Sequence
<220> FEATURE:
<223> OTHER INFORMATION: DNA sequence (LY2.55.4), for peptide L1-15
      (with LE) fused to the N-terminus of the heavy chain of
      Bevacizumab

<400> SEQUENCE: 24

```
atggcttgga tgatgctgct gcttggcctt ctcgcatacg gttccggagt cgatagcgcc     60
caacagaagt accagcctct ggacgaactg ataagaccc tgtacgatca gttcatgctg    120 caacagggc ttgagggcgg cggaggatcg ggcggtggtg gatccggcgg cggcggatcc    180
gaagtgcagc tcgtggagag cggggggcgga ctcgtgcagc cgggaggttc gctgagattg    240
tcctgtgccg cctccggtta cacctttacc aattacggga tgaactgggt ccgccaggcc    300
cccggaaagg gactggaatg ggtcggctgg atcaacacat ataccggaga gcccacctac    360
gccgcggact tcaagcggag attcaccttt tcactggata cgtcaaagtc aactgcatac    420
ctccagatga actcccttag gcggaagat accgccgtgt actactgcgc caagtacccg    480
cactattacg gtccagcca ttggtacttc gacgtctggg gacaggggac cctcgtgacc    540
gtcagcagcg cctccaccaa gggcccgtcc gtgttccctc ttgcgccgtc gtccaaaagc    600
acttccggcg gcactgccgc cctggctgc tcgtgaagg attacttccc ggaaccggtc     660
accgtgtcgt ggaactccgg agccctgact cgggtgtcc acccttccc tgcggtgctg    720 cagagctccg gtctgtactc cctctcttcc gtggtcacgg tgcccctc atcactggga    780 acccagacct acatctgcaa cgtgaaccac aagccctcaa acactaaggt cgacaagaaa    840
gtcgaaccga gtcgtgcga caagacccac acttgccctc cgtgcccggc tcccgagctg    900 ctgggggcc cttccgtgtt tttgttcccg ccgaaaccaa aggacactct gatgatcagc    960
cgcactccgg aagtgacctg tgtggtggtg gacgtgtccc acgaggaccc agaagtgaaa   1020
ttcaattggt acgtggatgg cgtggaagtg cacaacgcta agactaagcc cgcgaggaa   1080 cagtacaaca gcacttaccg ggtggtgtcg gtgctcaccg tgctgcacca agattggctc   1140
aacgggaagg agtacaagtg caaagtctcc aacaaggccc tgcccgcacc tattgaaaag   1200
```

```
accatcagca aggccaaggg acagccccgg gagccccagg tctacaccct gcctccctcg    1260
cgcgaagaga tgactaagaa ccaagtgtcc ctgacctgtc tggtcaaggg attctatcct    1320
tccgacattg ccgtggaatg ggagtccaac gggcagccag agaacaacta caagaccact    1380
ccacctgtgc tggactccga cgggtccttc ttcttgtact cgaagctgac cgtggacaag    1440
tcccggtggc agcagggaaa cgtgttcagc tgctccgtga tgcacgaggc cttgcataat    1500
cattacaccc aaaagtcgct gagcttgagc ccgggaaagt gataa                    1545

<210> SEQ ID NO 25
<211> LENGTH: 705
<212> TYPE: DNA
<213> ORGANISM: Artificial Sequence
<220> FEATURE:
<223> OTHER INFORMATION: DNA sequence (LY2.55.5), for the light chain of
      Bevacizumab

<400> SEQUENCE: 25
atggcctgga tgatgttgct tctcggactt ctcgcgtatg gatcaggggt ggactccgac      60
attcaaatga ctcagtcgcc atcgtccctc tcggcatccg tgggagacag agtgaccatc     120
acttgttccg cctcgcaaga catctccaac tacctgaact ggtaccagca gaagcccggg     180
aaggccccca aagtgctcat ctactttact tcctcactgc actccggggt gccaagccgc     240
tttagcggct ccggttctgg aaccgatttc accctgacca ttagctcact ccagccggaa     300
gatttcgcta cgtactactg ccagcagtat tcgaccgtgc cgtggacttt cggacagggt     360
accaaagtcg agatcaagcg gaccgtggcc gccccgagcg tgttcatttt cccgccttcc     420
gacgagcaac tcaagtccgg cactgcctcc gtggtctgcc tgctgaacaa tttctacccc     480
cgcgaggcta aggtccagtg gaaggtcgat aacgcactgc agtccggaaa cagccaagag     540
agcgtgaccg aacaggactc caaggactca acttactcgc tgagctccac cctgaccctg     600
tcgaaggccg actacgaaaa gcacaaagtg tacgcctgcg aagtgacaca tcagggcctg     660
tcatcccctg tcaccaagtc cttcaaccgg ggagagtgct gataa                    705
```

The invention claimed is:

1. A peptide-protein fusion molecule, wherein the peptide has an amino acid sequence selected from the group consisting of SEQ ID NOS: 7-12, and wherein said protein has an amino acid sequence of SEQ ID NO: 5.

2. The peptide-protein fusion molecule of claim 1, wherein the peptide-protein fusion molecule forms a homologous dimer, and wherein the dimer binds to both VEGF and Ang 2.

3. The peptide-protein fusion molecule of claim 1, wherein the peptide is fused to the N-terminal of the protein.

4. The peptide-protein fusion molecule of claim 1, wherein the peptide is fused to the C-terminal of the protein.

5. The peptide-protein fusion molecule of claim 1, further comprising a peptide linker.

* * * * *